(12) United States Patent
Obaishi et al.

(10) Patent No.: US 7,998,948 B2
(45) Date of Patent: *Aug. 16, 2011

(54) PHARMACEUTICAL COMPOSITION FOR TREATING ESOPHAGEAL CANCER

(75) Inventors: Hiroshi Obaishi, Tsukuba (JP); Takayuki Nakagawa, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/315,291

(22) Filed: Dec. 1, 2008

(65) Prior Publication Data

US 2009/0176797 A1 Jul. 9, 2009

(30) Foreign Application Priority Data

Nov. 30, 2007 (JP) ................................. 2007-311411

(51) Int. Cl.
*A61K 31/496* (2006.01)
*A61K 31/444* (2006.01)
*A61K 31/397* (2006.01)

(52) U.S. Cl. ............... 514/210.18; 514/253.13; 514/318

(58) Field of Classification Search ........................ None
See application file for complete search history.

(56) References Cited

U.S. PATENT DOCUMENTS

| | | | |
|---|---|---|---|
| 6,790,852 B2 | 9/2004 | Brandt et al. | |
| 7,253,286 B2 | 8/2007 | Funahashi et al. | |
| 7,425,564 B2 | 9/2008 | Fujiwara et al. | |
| 7,531,532 B2 | 5/2009 | Matsushima et al. | |
| 7,652,022 B2 | 1/2010 | Floersheimer et al. | |
| 7,855,290 B2 * | 12/2010 | Matsushima et al. | ......... 544/295 |
| 2003/0199691 A1 | 10/2003 | Brandt et al. | |
| 2004/0053908 A1 | 3/2004 | Funahashi et al. | |
| 2004/0214874 A1 | 10/2004 | Brandt et al. | |
| 2004/0242603 A1 | 12/2004 | Fujiwara et al. | |
| 2005/0009840 A1 | 1/2005 | Cui et al. | |
| 2005/0009842 A1 | 1/2005 | Zemlicka et al. | |
| 2005/0014753 A1 | 1/2005 | Ding et al. | |
| 2005/0245530 A1 | 11/2005 | Borzilleri et al. | |
| 2005/0277652 A1 | 12/2005 | Matsushima et al. | |
| 2006/0252777 A1 | 11/2006 | Kim et al. | |
| 2008/0214815 A1 | 9/2008 | Nagai et al. | |
| 2008/0300273 A1 | 12/2008 | Christensen et al. | |
| 2008/0318924 A1 | 12/2008 | Matsushima et al. | |
| 2008/0319188 A1 | 12/2008 | Matsushima et al. | |
| 2009/0227556 A1 | 9/2009 | Obaishi | |
| 2010/0075944 A1 | 3/2010 | Matsushima et al. | |
| 2010/0311972 A1 | 12/2010 | Nagai | |

FOREIGN PATENT DOCUMENTS

| | | |
|---|---|---|
| EP | 1 411 046 A1 | 4/2004 |
| EP | 1 415 987 A1 | 5/2004 |
| EP | 1 473 043 A1 | 11/2004 |
| EP | 1 506 962 A2 | 2/2005 |
| EP | 1 719 762 A1 | 11/2006 |
| EP | 1 719 763 A1 | 11/2006 |
| EP | 1 889 836 A1 | 2/2008 |
| EP | 2 058 302 A1 | 5/2009 |
| EP | 2 119 706 A1 | 11/2009 |
| JP | 2007-153894 | 6/2007 |
| JP | 2007-153894 A | 6/2007 |
| WO | WO-02/32872 A1 | 4/2002 |
| WO | WO-02/096361 A2 | 12/2002 |
| WO | WO-03/000660 A1 | 1/2003 |
| WO | WO-03/087026 A1 | 10/2003 |
| WO | WO-03/099771 A2 | 12/2003 |
| WO | WO 2004/030524 A2 | 4/2004 |
| WO | WO-2004/076412 A2 | 9/2004 |
| WO | WO-2004/089286 A2 | 10/2004 |
| WO | WO-2005/004607 A1 | 1/2005 |
| WO | WO-2005-004808 A2 | 1/2005 |
| WO | WO-2005/005378 A2 | 1/2005 |
| WO | WO-2005/005389 A2 | 1/2005 |
| WO | WO-2005/010005 A1 | 2/2005 |
| WO | WO-2005/016920 A1 | 2/2005 |
| WO | WO-2005/030140 A2 | 4/2005 |
| WO | WO-2005/040154 A1 | 5/2005 |
| WO | WO-2005/082854 A1 | 9/2005 |
| WO | WO-2005/082855 A1 | 9/2005 |
| WO | WO 2005/115478 A2 | 12/2005 |
| WO | WO-2005/117867 A2 | 12/2005 |
| WO | WO-2006/004636 A1 | 1/2006 |
| WO | WO-2006/014325 A2 | 2/2006 |

(Continued)

OTHER PUBLICATIONS

Berge et al., "Pharmaceutical Salts", Journal of Pharmaceutical Sciences, vol. 66, No. 1, pp. 1-19, 1997.

(Continued)

*Primary Examiner* — Phyllis G. Spivack
(74) *Attorney, Agent, or Firm* — Birch, Stewart, Kolasch & Birch, LLP

(57) ABSTRACT

A method of treating esophageal cancer, containing the step of administering to a patient suffering from esophageal cancer, a compound or a salt thereof, wherein the compound is: N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide, N-[4-({2-[(azetidin-1-ylcarbonyl)amino]pyridin-4-yl}oxy)-2-fluorophenyl]-N'-(4-fluorophenyl)cyclopropane-1,1-dicarboxamide, N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide, N-(2,5-difluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide, N-(2,5-difluoro-4-{[2-({[methyl(1-methyl-piperidin-4-yl)amino]carbonyl}amino)pyridin-4-yl]oxy}phenyl)-N'-(4-fluorophenyl)-cyclopropane-1,1-dicarboxamide, or N-(2,5-difluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide.

1 Claim, No Drawings

FOREIGN PATENT DOCUMENTS

| WO | 2007/023768 A1 | 3/2007 |
|---|---|---|
| WO | WO 2008/026577 A1 | 3/2008 |
| WO | 2008/102870 A1 | 8/2008 |

OTHER PUBLICATIONS

English translation of International Preliminary Report on Patentability (IPRP—Chapter I) issued in International Application No. PCT/JP2007/066185 dated Mar. 5, 2009 (6 pages).

Matsushima et al., "Preparation of pyridine and pyrimidine derivatives as inhibitors of hepatocyte growth factor receptor (HGFR)", Hcaplus 2005:977021, Sep. 9, 2005.

Naran et al., "Inhibition of HGF/MET as therapy for malignancy", Expert Opinion Ther. Targets, vol. 13, No. 5, pp. 569-581, 2009.

English translation of WO 2008/102870 published Aug. 28, 2008.

To et al., "The roles of hepatocyte growth factor/scatter factor and met receptor in human cancers", Oncology Reports, 5, pp. 1013-1024 (1998).

Rosen et al., "Scatter Factor and angiogenesis", Advances in Cancer Research, vol. 67, pp. 257-279 (1995).

Maehara et al., "NK4, a four-kringle antagonist of HGF, inhibits spreading and invasion of human pancreatic cancer cells", British Journal of Cancer, vol. 84, No. 6, pp. 864-873. (2001).

Matsumoto et al., "NK4 (HGF-antagonist/angiagenesis inhbitor) in cancer biology and therapeutics", Cancer Sci, vol. 94, pp. 321-327 (2003).

Kolibaba et al., "Protein tyrosine kinases and cancer", B. B. A., 1333, F217-F248, (Jul. 1997), Portland, OR.

Sheijen et al., "Tyrosine kinase oncogenes in normal hematopoiesis and hematological disease", Oncogene, 21, 3314-333L(2002), Boston, MA.

Blume-Jensen et al., "Activation of the human c-kit product by ligand-induced dimerization mediates circular actin reorganization and chemotaxis", The EMBO Journal, 10, 4121-4128, (1991), Thousand Oaks, CA and Sweden.

Lev et al., "A specific combination of substrates is involved in signal transduction by the kit-encoded receptor" The EMBO Journal, 10, 647-654, (1991), Isreal.

Wang et al., "The Expression of the Proto-Oncogene C-Kit in the Blast Cells of Acute Myeloblastic Leukemia", Leukemia, 3, 699-702, (1989), Toronto, Canada and Cambridge, MA.

Kanakura et al., "Expression, Function and Activation of The Protooncogen c-kit Product in Human Leukemia Cells", Leukemia and Lymphoma, 10, 35-41, (1993), Osaka, Japan.

Ikeda et al., "Expression and Functional Role of the Proto-oncogene c-kit in Acute Myeloblastic Leukemia Cells", Blood, 78, 2962-2968, (1991).

Ikeda et al., "Changes in phenotype and proliferative potential of human acute myeloblastic leukemia cells in culture with stem cell factor", Experimental Hematology, 21, 1686-1694, (Aug. 1993), Osaka, Japan.

Furitsu et al., "Identification of Mutations in the Coding Sequence of the Proto-oncogene c-kit in a Human Mast Cell Leukemia Cell Line Causing Ligand-independent Activation of c-kit Product", J. Clin. Invest., 92, 1736-1744, (1993), Osaka, Japan; Rochester; MN and Adelaide, 'South Australia.

Hibi et al , "Coexpression of the stem cell factor and the c-kit genes in small-cell lung cancer", Oncogene, 6, 2291-2296, (1991), Nagoya, Japan.

Sekido et al., "Preferential Expression of c-kit Protooncogene Transcripts in Small Cell Lung Cancer", Cancer Research, 51, 2416-2419, (May 1, 1991), Nagoya, Japan.

Lasota et al., "Mutations in Exons 9 and 13 of KIT Gene Are Rare Events in Gastrointestinal Stromal Tumors", American Journal of Pathology, 157, 1091-1095, (Oct. 2000), Washington, D.C.; Helsinki, Finland and Krakow, Poland.

Taniguchi et al., Effect of c-kit Mutation on Prognosis of Gastrointestinal Stomal Tumors, Cancer Research, 59, 4297-4300, (Sep. 1, 1999), Japan.

Strohmeyer et al., "Expression of the hst-1 and c-kit Protooncogenes in Human Testicular Germ Cell Tumors", Cancer Research, 51, 1811-1816, (Apr. 1, 1991), CA and Germany.

Tian et al., "Activating c-kit Gene Mutations in Human Germ Cell Tumors", American Journal of Pathology, 154, 1643-1647, (Jun. 1999), VA.

Tonary et al., "Lack of Expression of c-Kit in Ovarian Cancers Is Associated With Poor Prognosis", Int. J. Cancer (Pred. Oncol.), 89, 242-250, (2000), Ottawa, Canada.

Natali et al., "Breat Cancer Is Associated With Loss of the c-kit lkit Oncogene Product". Int. J. Cancer, 52, 713-717, (1992), Rome, Italy.

Hines et al., "Coexpression of the c-kit and Stem Cell Factor Genes in Breast Carcinomas", Cell Growth & Differentiation, 6, 769-779, (Jun. 1995), Richmond, VA.

Berdel et al., "Recombinant Human Stem Cell Factor Stimulates Growth of a Human Glioblastoma Cell Line Expressing c-kit Protooncogene", Cancer Research, 52, 3498-3502, (Jun. 15, 1992), Germany.

Cohen et al., "Expression of Stem Cell Factor and c-kit in Human Neuroblastoma", Blood, 84, 3465-3472, (1994).

Bellone et al., "Growth Stimulation of Colorectal Carcinoma Cells Via the c-Kit Receptor Is Inhibited by TGF-β1", Journal of Cellular Physiology, 172, 1-11, (1997), Torino, Italy and Philadelphia, PA.

Hamel et al., "The road less travelled: c-kit and stem cell factor", Journal of Neuro-Oncology, 35, 327-333, (1997), Hamburg, Germany and San Francisco, CA.

Kitamura et al., "Regulation of Development, Survival and Neoplastic Growth of Mast Cells through the c-kit Receptor", Int. Arch. Allergy Immunol., 107, 54-56, (1995), Osaka, Japan.

Metcalfe, "Classification and Diagnosis of Mastocytosis: Current Status", J. Invest. Derm., 96, 2S-4S, (1991), Bethesda, MD.

Golkar et al., "Mastocytosis", The Lancet, 349, 1379-1385, (1997).

Nagata et al., "Elevated expression of the proto-oncogene c-kit in patients with mastocytosis", Leukemia, 12, 175-181, (1998), Bethesda, MD.

Longley et al., "Altered Metabolims of Mast-Cell Growth Factor (c-kit Ligand) in Cutaneous Mastocytosis", New England Journal of Medicine, 328, 1302-1307, (May 6, 1993).

Longley et al., "Somatic c-KIT activating mutation in urticaria pigmentosa and aggressive mastocytosis: establishment of clonality in a human mast cell neoplasm", Nature Genetics, 12, 312-314, (Mar. 1996).

Thomas et al., "The Eosinophil and its Role in Asthma", Gen. Pharmac., 27, 593-597, (1996), Southampton, UK.

Metcalfe et al., "Mast Cells", Physiological Reviews, 77, 1033-1079, (Oct. 1997), Tel Aviv, Israel.

Naclerio et al., "Rhinitis and Inhalant Allergens", JAMA, 278, 1842-1848, (Dec. 10, 1997).

Meltzer, "Thepharmacological basis for the treatment of perennial allergic rhinitis and non-allergic rhinitis with topical corticosteroids", Allergy, 52, 33-40, (1997), San Diego, CA.

Okayama et al., "Activation of Eosinophils with Cytokines Produced by Lung Mast Cells", International Archives of Allergy and Immunology, 114, 75-77, (1997), Maebashi, Japan; Southampton, UK and Adelaide, Australia.

Okayama et al., "Human lung mast cells are enriched in the capacity to produce granulocyte-macrophage colony-stimulating factor in response to IgE-dependent stimulation", Eur. J. Immunol., 28, 708-715, (1998), Maebashi, Japan, Adelaide, Australia and Southampton, GB.

Metcalf, "Lineage commitment in the progeny of murine hematopoietic preprogenitor cells: Influence of thrombopoietin and interleukin", Proc. Natl. Acad. Sci., 95, 6408-6412, (May 1998), Victoria, Australia.

Kay et al , "Eosinophils and Eosinophil-Associated Cytokines in Allergic Inflammation", International Archives of Allergy and Immunology, 113, 196-199, (1997), London, UK.

Hogaboam et al., "Novel Role of Transmembrane SCF for Mast Cell Activation and Eotaxin Production in Mast Cell-Fibroblast Interactions", The Journal of Immunology, 160, 6166-6171, Feb. 17, 1998), Ann Arbor, MI and Frederick, MD.

Luckas et al., "Stem Cell Factor (c-kit Ligand) Influences Eosinophil Recruitment and Histamine Levels in Allergic Airway Inflammation", The Journal of Immunology, 156, 3945-3951, (Feb. 28, 1996), Ann Arbor, MI; Frederick, MD and New Haven, CT.

Folkman et al., "Angiogenesis", The Journal of Biological Chemistry, 267, 10931-10934, (1992), Boston, MA.
Jakeman et al., "Developmental Expression of Binding Sites and Messenger Ribonucleic Acis for Vascular Endothelial Growth Factor Suggests a Role for This Protein in Vasculogenesis and Angiogenesis", Endocrinology, 133, 848-859, (1993), San Francisco, CA.
Folkman, "Clinical Applications of Research on Angiogenesis", The New England Journal of Medicine, 333, 1757-1763, (Dec. 28, 1995).
Folkman, "What Is the Evidence That Tumors Are Angiogenesis Dependent?", Journal of the National Cancer Institute, 82, 4-6, (Jan. 3, 1990), Boston, MA.
Ferrara et al., "Molecular and Biological Properties of the Vascular Endothelial Growth Factor Family of Proteins", Endocrine Reviews, 13, 18-32, (1992), San Francisco, CA.
Plate et al., "Vascular endothelial growth factor is a potential tumour angiogenesis factor in human gliomas in vivo", Letter to Nature, 359, 845-848, 1992), Germany.
Plate et al., "Up-Regulation of Vascular Endothelial Growth Factor and Its Cognate Receptors in a Rat Glioma Model of Tumor Angiogenesis", Cancer Research, 53, 5822-5827, (Dec. 1, 1993), Germany.
Berkman et al., "Expression of the Vascular Permeability Factor/Vascular Endothelial Growth Factor Gene in Central Nervous System Neoplasms", The Journal of Clinical Investigation, 91, 153-159, (Jan. 1993), Bethesda, MD and Memphis, TN.
Nakamura et al., "Vascular Endothelial Growth Factor Is a Potent Angiogenic Factor in AIDS-Associated Kaposi's Sarcoma-Derived Spindle Cells", The Journal of Immnology, 158, 4992-5001, (Dec. 1997), Germany and CA.
Mustonen et al., "Endothelial Receptor Tyrosine Kinases Involved in Angiogenesis", The Journal of Cell Biology, 129, 895-898, (May 1995), Helsinki, Finland.
Bardella et al., "Truncated RON Tyrosine Kinase Drives Tumor Cell Progression and Abrogates Cell-Cell Adhesion Through E-Cadherin Transcriptional Repression", Cancer Research, 64, 5154-5161, (Aug. 1, 2004), Italy.
O'Toole et al., "Therapeutic Implications of a Human Neutralizing Antibody to the Macrophage-Stimulating Protein Receptor Tyrosine Kinase (RON), a c-MET Family Member", Cancer Research, 66, 9162-9170, (2006), Stonybrook, NY and Cincinnati, OH.
Carlomagno et al., "ZD6474, an Orally Available Inhibitor of KDR Tyrosine Kinase Activity, Efficiently Blocks Oncogenic RET Kinases", Cancer Research, 62, 7284-7290, (Dec. 15, 2002), Italy and UK.
Carlomagno et al., "BAY 43/9006 Inhibition of Oncogenic RET Mutants", Journal of National Cancer Institute, 98, 326-334, (Mar. 1, 2006).
Terman et al., "Identification of a new endothelial cell growth factok receptor tyrosine kinase", Oncogene, 6, 1677-1683, (1991), NY.
Park et al., "Homogeneous Proximity Tyrosine Kinase Assays: Scintillation Proximity Assay versus Homogeneous Time-Resolved Fluorescence", Analytical Biochemistry, 269, 94-104, (1999), Rahway, NJ.
Matthias Ebert et al., Coexpression of the *c-met* . . . , Cancer Research 54, pp. 5775-5778, 1994.
Hiroki Kuniyasu et al.; Frequent amplification . . . , Biochemical and Biophysical Research Communications, vol. 189, No. 1, pp. 227-232, Nov. 30, 1992.
Chi Liu et al., Overexpression of *c-met* . . . , Oncogene, 7, pp. 181-185, 1992.
Rola A. D. Ghoussoub et al.; Expression of *c-met* . . . , Cancer, 82, pp. 1513-1520, 1998.
Louis L. Pisters et al., C-met Proto-Oncogene Expression, The Journal of Urology, vol. 154, pp. 293-298, Jul. 1995.

Iwao Takanami et al., Hepatocyte Growth Factor . . . , Oncology, 53, pp. 392-397, 1996.
Laura Schmidt et al., Novel mutations of the MET . . . , Oncogene, 14, pp, 2343-2350, 1999.
Shahriar Koochekpour et al., Met and Hepatocyte Growth . . . , Cancer Research, 57, pp. 5391-5398, 1997.
Janos Tanyi et al., Evaluation of the Tyrosine . . . , Pathology Oncology Research, 5, pp. 187-191, 1999.
Yoshitaka Imaizumi et al., Expression of the c-Met . . . , Clinical Cancer Research, vol. 9, pp. 181-187, 2003.
Joachim Ulrich, "Crystallization-4.Crystal Characteristics", Kirk-Othmer Encyclopedia of Chemical Technology, Aug. 2002.
Sudha R. Vippagunta et al., "Crystalline Solids", Advanced Drug Delivery Reviews, 48, 2001, pp. 3-26.
Anthony R. West, "Solid Solutions", Solid State Chemistry and its applications, 1988, pp. 358 and 365.
E7050: "A novel orally active c-MET and VEGFR-2 tyrosine kinase inhibitor exhibited potent antitumor effect and prolongation of survival in preclinical mice model.", Nakagawa et al., Proceedings of the American Association for Cancer Research, vol. 49, p. 1154, #4845, 2008.
E7050: "A novel small molecule the c-MET and VEGFR-2 tyrosine kinase.", Obaishi et al., Proceedings of the American Association for Cancer Research, vol. 49, p. 1154, #4846, 2008.
"MET tyrosine kinase inhibitors" Nature Reviews Drug Discovery, vol. 7, Jun. 2008, p. 469.
Watson et al., "Inhibition of c-Met as a Therapeutic Strategy for Esophageal Adenocarcinoma," Neoplasia, vol. 8, No. 11, Nov. 2006, pp. 949-955.
English Translation of International Search Report and Written Opinion for PCT/IB2008/003880 issued Aug. 11, 2009.
H. Saeki et al., "Concurrent overexpression of Ets-1 and c-Met correlates with a phenotype of high cellular motility in human esophageal cancer", International Journal of Cancer, vol. 98, No. 1, pp. 8-13, 2002.
C. T. Miller et al., "Genomic amplification of MET with boundaries within fragile site FRA7G and upregulation of MET pathways in esophageal adenocarcinoma", Oncogene, vol. 25, No. 3, pp. 409-418, 2006.
International Preliminary Report on Patentability and Written Opinion of the International Searching Authority mailed Oct. 5, 2010 for International Application No. PCT/JP2009/052401 (Forms PCT/ISA/237, PCT/IB/338 and PCT/IB/373).
Extended European Search Report, dated Nov. 16, 2010, for European Application No. 07805959.9.
International Preliminary Report on Patentability for Application No. PCT/JP2006/316331, dated Feb. 26, 2008, with translation.
International Preliminary Report on Patentability, dated Feb. 24, 2009, for Application No. PCT/JP2007/066185.
International Search Report, dated Mar. 10, 2009, for Application No. PCT/JP2009/052401.
Smolen, "Amplification of MET May Identify a Subset of Cancers With Extreme Sensitivity to the Selective Tyrosine Kinase Inhibitor PHA-665752", PNAS, vol. 103, No. 7, Feb. 14, 2005.
European Office Action issued on Feb. 11, 2011 in related European Patent Application No. 05 719 973.9.
Nicolaus, "Synbiotic Approach to Drug Design," Decision Making in Drug Research, Jan. 1, 1983, pp. 173-186, Raven Press, New York.
Extended European Search Report issued on Apr. 28, 2011 in European Patent Application No. 09 71 3617.
S. Neidle, ed. Cancer Drug Design and Discovery, (Elsevier/Academic Press), pp. 427-431 (2008).

* cited by examiner

PHARMACEUTICAL COMPOSITION FOR TREATING ESOPHAGEAL CANCER

TECHNICAL FIELD

The present invention relates to a pharmaceutical composition for treating esophageal cancer comprising a pyridine and pyrimidine derivative, a salt thereof or a hydrate of the foregoing having hepatocyte growth factor receptor inhibitory action, anti-tumor action, angiogenesis inhibitory action, cancer metastasis inhibitory action or the like.

BACKGROUND ART

Overexpression of hepatocyte growth factor receptor (hereafter referred to as "HGFR") is reported in various kinds of tumors such as a pancreatic cancer, a gastric cancer, a colorectal cancer, a breast cancer, a prostate cancer, a lung cancer, a renal cancer, a brain tumor, an ovarian cancer, an esophageal cancer (non-patent documents 1 and 5). HGFR expressed in these cancer cells is considered to be involved in cancer malignancy (aberrant growth, invasion or enhanced metastasis), because HGFR cause autophosphorylation of intracellular tyrosine kinase constitutively or upon stimulation by hepatocyte growth factor (hereafter referred to as HGF).

It is also reported that HGFR is expressed in vascular endothelial cells and is involved in tumor angiogenesis since HGF stimulates HGFR to facilitate proliferation and migration of vascular endothelial cells (non-patent document 2).

Furthermore, NK4, an antagonistic peptide for HGF, is reported to block HGF-HGFR signal to inhibit invasion of cancer cells and tumor angiogenesis (non-patent documents 3 and 4).

Therefore, a compound having inhibitory activity against HGFR is expected to be useful as an anti-tumor agent, an angiogenesis inhibitor or an inhibitor for cancer metastasis.

On the other hand, patent document 1 discloses low-molecular compounds having inhibitory activity against HGFR.

[Patent document 1] WO 2007/023768

[Non-patent document 1] Oncology Reports, 5, 1013-1024 (1998)

[Non-patent document 2] Advances in Cancer Research, 67, 257-279 (1995)

[Non-patent document 3] British Journal of Cancer, 84, 864-873 (2001)

[Non-patent document 4] Cancer Sci., 94, 321-327 (2003)

[Non-patent document 5] Oncogene, 25(3), 409-418 (2006)

DISCLOSURE OF THE INVENTION

Problems to be Solved by the Invention

The object of the invention is to discover a pharmaceutical composition for treating esophageal cancer by inhibiting aberrant growth, morphological change and motility facilitation of cells via HGFR in vivo.

Means for Solving the Problems

As a result of diligent studies, the inventors have discovered that a novel pyridine and pyrimidine derivative represented by the general formula (I) below, a salt thereof or a hydrate of the foregoing has excellent inhibitory action against HGFR, and completed the present invention.

Namely, the present invention provides [1] to [24] below:

[1] A pharmaceutical composition for treating esophageal cancer, comprising a compound represented by the following formula, a salt thereof or a hydrate of the foregoing:

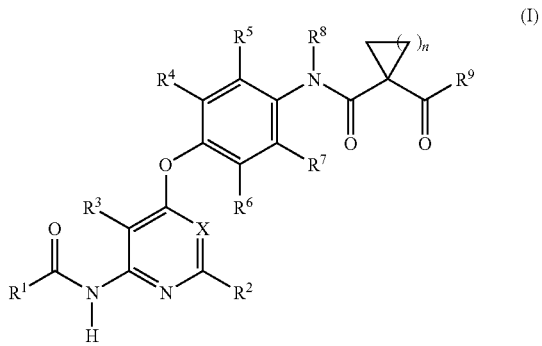

(I)

wherein $R^1$ represents a 3- to 10-membered non-aromatic heterocyclic group wherein the group is limited to a group having nitrogen as a ring constituent atom and the nitrogen having a bonding hand, or a group represented by the formula —$NR^{11a}R^{11b}$, wherein $R^{11a}$ and $R^{11b}$ may be the same or different and each represents hydrogen, $C_{1-6}$ alkyl, $C_{3-6}$ alkenyl, $C_{3-6}$ alkynyl, $C_{3-10}$ cycloalkyl, $C_{6-10}$ aryl, 5- to 10-membered heteroaryl or a 4- to 10-membered non-aromatic heterocyclic group, and $R^{11a}$ and $R^{11b}$ may be substituted with a substituent selected from Substituent Group A or Substituent Group B and $R^1$ may be substituted with a substituent selected from Substituent Group A or Substituent Group B;

$R^2$ and $R^3$ represent hydrogen;

$R^4$, $R^5$, $R^6$ and $R^7$ may be the same or different and each represents hydrogen, halogen, hydroxyl, cyano, trifluoromethyl, $C_{1-6}$ alkyl, $C_{2-6}$ alkenyl, $C_{2-6}$ alkynyl, $C_{1-6}$ alkoxy, amino, mono-$C_{1-6}$ alkylamino, di-$C_{1-6}$ alkylamino or a group represented by the formula —CO—$R^{12}$, wherein $R^{12}$ represents hydrogen, hydroxyl, $C_{1-6}$ alkyl, $C_{1-6}$ alkoxy, amino, mono-$C_{1-6}$ alkylamino or di-$C_{1-6}$ alkylamino;

$R^8$ represents hydrogen or $C_{1-6}$ alkyl;

$R^9$ represents a 3- to 10-membered non-aromatic heterocyclic group wherein the group is limited to a group having nitrogen as a ring constituent atom and the nitrogen having a bonding hand, or a group represented by the formula —$NR^{11a}R^{11b}$, wherein $R^{11a}$ and $R^{11b}$ represent the same meaning as described above and $R^9$ may be substituted with a substituent selected from Substituent Group A or Substituent Group B;

n represents an integer of 1 or 2; and

X represents a group represented by the formula —$C(R^{10})$= or nitrogen, wherein $R^{10}$ represents hydrogen, halogen, cyano, $C_{1-6}$ alkyl, $C_{2-6}$ alkenyl, $C_{2-6}$ alkynyl or a group represented by the formula —CO—$R^{12}$, wherein $R^{12}$ represents the same meaning as recited above;

wherein Substituent Group A consists of halogen, hydroxyl, mercapto, nitro, cyano and oxo;

wherein Substituent Group B consists of $C_{1-6}$ alkyl, $C_{2-6}$ alkenyl, $C_{2-6}$ alkynyl, $C_{3-10}$ cycloalkyl, $C_{6-10}$ aryl, 5- to 10-membered heteroaryl, a 3- to 10-membered non-aromatic heterocyclic group, $C_{1-6}$ alkoxy, $C_{3-6}$ alkenyloxy, $C_{3-6}$ alkynyloxy, $C_{3-10}$ cycloalkoxy, $C_{6-10}$ aryloxy, 5- to 10-membered heteroaryloxy, 4- to 10-membered non-aromatic heterocyclicoxy, $C_{1-6}$ alkylthio, $C_{3-6}$ alkenylthio, $C_{3-6}$ alkynylthio, $C_{3-10}$ cycloalkylthio, $C_{6-10}$ arylthio, 5- to 10-membered heteroarylthio, 4- to 10-membered non-aromatic heterocyclicthio and a group represented by the formula -$T^1$-$T^2$-$T^3$, and each group in Substituent Group B may be substituted with a substituent selected from Substituent Group C, wherein $T^1$ represents a direct bond or $C_{1-6}$ alkylene, $T^2$ represents carbonyl, sulfinyl, sulfonyl, a group represented by the formula —C(=O)—O—, a group represented by the formula —O—C(=O)—, a group represented by the formula —SO₂—O—, a group represented by the formula —O—SO₂—, a group represented by the formula —NR^{T1}—, a group represented by the formula —C(=O)—NR^{T1}—, a group represented by the formula —NR^{T1}—C(=O)—, a group represented by the formula —SO₂—NR^{T1}— or a group represented by the formula —NR^{T1}—SO₂—, $T^3$ represents hydrogen, $C_{1-6}$ alkyl, $C_{3-6}$ alkenyl, $C_{3-6}$ alkynyl, $C_{3-10}$ cycloalkyl, $C_{6-10}$ aryl, 5- to 10-membered heteroaryl or a 4- to 10-membered non-aromatic heterocyclic group, and $R^{T1}$ represents hydrogen or $C_{1-6}$ alkyl; and wherein Substituent Group C consists of halogen, hydroxyl, mercapto, nitro, cyano, oxo, $C_{1-6}$ alkyl, $C_{2-6}$ alkenyl, $C_{2-6}$ alkynyl, $C_{3-10}$ cycloalkyl, $C_{6-10}$ aryl, 5- to 10-membered heteroaryl, a 3- to 10-membered non-aromatic heterocyclic group, $C_{1-6}$ alkoxy, $C_{1-6}$ alkylthio, mono-$C_{1-6}$ alkylamino and di-$C_{1-6}$ alkylamino.

[2] The pharmaceutical composition for treating esophageal cancer of [1], wherein $R^1$ represents a 3- to 10-membered non-aromatic heterocyclic group optionally substituted with a substituent selected from Substituent Group A or Substituent Group B recited in [1], wherein the group is limited to a group having nitrogen as a ring constituent atom and the nitrogen having a bonding hand.

[3] The pharmaceutical composition for treating esophageal cancer of [1], wherein $R^1$ represents a group represented by the formula (II):

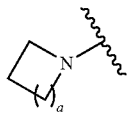

(II)

wherein a represents an integer of 1 to 4;
or a group represented by the formula (III):

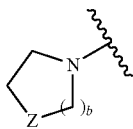

(III)

wherein b represents an integer of 1 to 3, and Z represents oxygen, sulfur, carbonyl, sulfonyl, or a group represented by the formula —NR^Z—, wherein $R^Z$ represents hydrogen or $C_{1-6}$ alkyl, and the groups represented by the formula (II) or (III) may be substituted with a substituent selected from Substituent Group A or Substituent Group B recited in [1].

[4] The pharmaceutical composition for treating esophageal cancer of [1], wherein $R^1$ represents azetidin-1-yl optionally substituted with a substituent selected from Substituent Group D, pyrrolidin-1-yl optionally substituted with a substituent selected from Substituent Group D, piperidin-1-yl optionally substituted with a substituent selected from Substituent Group D, azepan-1-yl optionally substituted with a substituent selected from Substituent Group D, piperazin-1-yl optionally substituted with a substituent selected from Substituent Group D, diazepan-1-yl optionally substituted with a substituent selected from Substituent Group D, morpholin-4-yl optionally substituted with a substituent selected from Substituent Group D, thiomorpholin-4-yl optionally substituted with a substituent selected from Substituent Group D, 1,1-dioxothiomorpholin-4-yl optionally substituted with a substituent selected from Substituent Group D, wherein Substituent Group D consists of halogen, hydroxyl, mercapto, cyano, formyl, oxo, $C_{1-6}$ alkyl, $C_{3-10}$ cycloalkyl, $C_{1-6}$ alkoxy, amino, mono-$C_{1-6}$ alkylamino, di-$C_{1-6}$ alkylamino, azetidinyl, pyrrolidinyl, piperidinyl, piperazinyl, diazepanyl and a group represented by -$T^4$-$T^5$, wherein $T^4$ represents carbonyl or sulfonyl, and $T^5$ represents $C_{1-6}$ alkyl, $C_{3-10}$ cycloalkyl, azetidinyl, pyrrolidinyl, piperidinyl, hydroxyl, $C_{1-6}$ alkoxy, amino, mono-$C_{1-6}$ alkylamino or di-$C_{1-6}$ alkylamino, where each group included in Substituent Group D may be substituted with hydroxyl, $C_{1-6}$ alkyl, di-$C_{1-6}$ alkylamino, azetidinyl or pyrrolidinyl.

[5] The pharmaceutical composition for treating esophageal cancer of [1], wherein $R^1$ represent azetidin-1-yl optionally substituted with a substituent selected from Substituent Group E, pyrrolidin-1-yl optionally substituted with a substituent selected from Substituent Group E, piperidin-1-yl optionally substituted with a substituent selected from Substituent Group E, piperazin-1-yl optionally substituted with a substituent selected from Substituent Group E, diazepan-1-yl optionally substituted with a substituent selected from Substituent Group E or morpholin-4-yl optionally substituted with a substituent selected from Substituent Group E, wherein Substituent Group E consists of methyl, ethyl, dimethylamino, azetidinyl, pyrrolidinyl, piperidinyl and piperazinyl, where each group included in Substituent Group E may be substituted with hydroxyl, methyl, dimethylamino, azetidinyl, pyrrolidinyl or piperidinyl.

[6] The pharmaceutical composition for treating esophageal cancer of [1], wherein $R^1$ represents azetidin-1-yl optionally substituted with a substituent selected from Substituent Group G, pyrrolidin-1-yl optionally substituted with a substituent selected from Substituent Group G, piperidin-1-yl optionally substituted with a substituent selected from Substituent Group G or piperazin-1-yl optionally substituted with a substituent selected from Substituent Group G, wherein Substituent Group G consists of dimethylamino, azetidinyl, pyrrolidinyl, piperidinyl, piperazinyl, dimethylaminomethyl, dimethylaminoethyl, azetidin-1-ylmethyl, pyrrolidin-1-ylmethyl and piperidin-1-ylmethyl, where each group included in Substituent Group G may be substituted with methyl or dimethylamino.

[6-1] The pharmaceutical composition for treating esophageal cancer of [1], wherein $R^1$ represents azetidin-1-yl optionally substituted with a substituent selected from Substituent Group G-1, pyrrolidin-1-yl optionally substituted with a substituent selected from Substituent Group G-1, piperidin-1-yl optionally substituted with a substituent selected from Substituent Group G-1 or piperazin-1-yl optionally substituted with a substituent selected from Substituent Group G-1, wherein Substituent Group G-1 consists of azetidinyl, pyrrolidinyl, piperidinyl, piperazinyl, dimethylaminomethyl, dimethyl aminoethyl, azetidin-1-ylmethyl, pyrrolidin-1-ylmethyl and piperidin-1-ylmethyl, where each group included in Substituent Group G-1 may be substituted with methyl or dimethylamino.

[6-2] The pharmaceutical composition for treating esophageal cancer of [1], wherein $R^1$ represents azetidin-1-yl having dimethylamino, pyrrolidin-1-yl having dimethylamino or piperidin-1-yl having dimethylamino.

[6-3] The pharmaceutical composition for treating esophageal cancer of [1], wherein $R^1$ represents azetidin-1-yl optionally substituted with a substituent selected from Substituent Group G-2, pyrrolidin-1-yl substituted with a substituent selected from Substituent Group G-2 or piperidin-1-yl substituted with a substituent selected from Substituent Group G-2, wherein Substituent Group G-2 consists of hydroxyl, methoxy, hydroxymethyl and dimethylaminoacetoxy.

[6-4] The pharmaceutical composition for treating esophageal cancer of [1], wherein $R^1$ represents [2-(dimethylamino)ethyl]piperazin-1-yl, 4-pyrrolidin-1-ylpiperidin-1-yl, 4-[(dimethylamino)methyl]piperidin-1-yl, 4-azetidin-1-ylpiperidin-1-yl, 4-[3-(dimethylamino)azetidin-1-yl]piperidin-1-yl, 4-(4-methylpiperazin-1-yl)piperidin-1-yl, 4-(1-methylpiperidin-4-yl)piperazin-1-yl, 4-(1-methylazetidin-3-yl)piperazin-1-yl, 4-(dimethylamino)piperidin-1-yl, 4-(azetidin-1-ylmethyl)piperidin-1-yl, 4-(pyrrolidin-1-ylmethyl)piperidin-1-yl, (3S)-3-(dimethylamino)pyrrolidin-1-yl, (3R)-3-(dimethylamino)pyrrolidin-1-yl, azetidin-1-yl, pyrrolidin-1-yl, morpholin-4-yl, 4-methylpiperazin-1-yl, 3-hydroxyazetidin-1-yl, 1,3'-biazetidin-1'-yl, 3-(hydroxymethyl)azetidin-1-yl, 3-(dimethylamino)azetidin-1-yl, 3-[(dimethylamino)methyl]azetidin-1-yl, 4-hydroxypiperidin-1-yl, 4-(hydroxymethyl)piperidin-1-yl, (3R)-3-hydroxypyrrolidin-1-yl, (3S)-3-hydroxypyrrolidin-1-yl, 3-(azetidin-1-ylmethyl)azetidin-1-yl or 3-(2-dimethylaminoacetoxy)azetidin-1-yl.

[7] The pharmaceutical composition for treating esophageal cancer of [1], wherein $R^1$ represents a group represented by the formula —$NR^{11a}R^{11b}$, wherein $R^{11a}$ and $R^{11b}$ represent the same meaning as recited in [1].

[8] The pharmaceutical composition for treating esophageal cancer of [1], wherein $R^1$ represents a group represented by the formula —$NR^{11c}R^{11d}$, wherein $R^{11c}$ represents hydrogen or $C_{1-6}$ alkyl, and $R^{11d}$ represents $C_{1-6}$ alkyl or a group represented by the formula (IV):

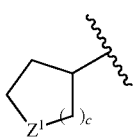

(IV)

wherein c represents an integer of 1 to 3, and $Z^1$ represents oxygen, sulfur, carbonyl, sulfonyl or a group represented by the formula —$NR^{Z1}$—, wherein $R^{Z1}$ represents hydrogen or $C_{1-6}$ alkyl, and $R^{11d}$ may be substituted with a substituent selected from Substituent Group A or Substituent Group B recited in [1].

[9] The pharmaceutical composition for treating esophageal cancer of [1], wherein $R^1$ represents a group represented by the formula —$NR^{11e}R^{11f}$, wherein $R^{11e}$ represents hydrogen or $C_{1-6}$ alkyl, and $R^{11f}$ represents $C_{1-6}$ alkyl, pyrrolidin-3-yl, piperidin-3-yl, piperidin-4-yl or tetrahydropyran-4-yl, and $R^{11f}$ may be substituted with a substituent selected from Substituent Group D recited in [4].

[10] The pharmaceutical composition for treating esophageal cancer of [1], wherein $R^1$ represents a group represented by the formula —$NR^{11g}R^{11h}$, wherein $R^{11g}$ represents hydrogen or methyl, and $R^{11h}$ represents n-propyl, n-butyl, pyrrolidin-3-yl, piperidin-3-yl, piperidin-4-yl or tetrahydropyran-4-yl, and $R^{11h}$ may be substituted with a substituent selected from Substituent Group F, wherein Substituent Group F consists of methyl, ethyl, n-propyl, acetyl, dimethylamino, diethylamino, azetidinyl, pyrrolidinyl and piperazinyl, where each group included in Substituent Group F may be substituted with methyl or dimethylamino.

[11] The pharmaceutical composition for treating esophageal cancer of [1], wherein $R^1$ represents a group represented by the formula —$N(CH_3)R^{11i}$, wherein $R^{11i}$ represents n-propyl, n-butyl, pyrrolidin-3-yl or piperidin-4-yl, and $R^{11i}$ may be substituted with a substituent selected from Substituent Group H, wherein Substituent Group H consists of dimethylamino, diethylamino, dimethylaminoethyl, dimethylaminopropyl and 1-methylazetidin-3-yl.

[12] The pharmaceutical composition for treating esophageal cancer of [1], wherein $R^1$ represents a group represented by the formula —$N(CH_3)R^{11j}$, wherein $R^{11j}$ represents 1-methylpiperidin-4-yl or 1-ethylpiperidin-4-yl.

[12-1] The pharmaceutical composition for treating esophageal cancer of [1], wherein $R^1$ represents a group represented by the formula —$N(CH_3)R^{11k}$, wherein $R^{11k}$ represents 3-(dimethylamino)propyl or 1-[2-(dimethylamino)ethyl]piperidin-4-yl.

[12-2] The pharmaceutical composition for treating esophageal cancer of [1], wherein $R^1$ represents methyl(1-methylpiperidin-4-yl)amino, (1-ethylpiperidin-4-yl)(methyl)amino, [3-(dimethylamino)propyl](methyl)amino or {1-[2-(dimethylamino)ethyl]piperidin-4-yl}(methyl)amino.

[13] The pharmaceutical composition for treating esophageal cancer of any one of [1] to [12-2], wherein $R^4$, $R^5$, $R^6$ and $R^7$ may be the same or different and each represents hydrogen, halogen or $C_{1-6}$ alkyl.

[14] The pharmaceutical composition for treating esophageal cancer of any one of [1] to [13], wherein $R^8$ represents hydrogen.

[15] The pharmaceutical composition for treating esophageal cancer of any one of [1] to [14], wherein X represents a group represented by the formula —$C(R^{10a})$=, wherein $R^{10a}$ represents hydrogen, halogen or cyano.

[16] The pharmaceutical composition for treating esophageal cancer of any one of [1] to [14], wherein X represents nitrogen.

[17] The pharmaceutical composition for treating esophageal cancer of any one of [1] to [16], wherein n represents 1.

[18] The pharmaceutical composition for treating esophageal cancer of any one of [1] to [17], wherein $R^9$ represents mono-$C_{1-6}$ alkylamino optionally substituted with a substituent selected from Substituent Group A or Substituent Group B recited in [1], mono-$C_{3-10}$ cycloalkylamino optionally substituted with a substituent selected from Substituent Group A or Substituent Group B recited in [1], mono-$C_{6-10}$ arylamino optionally substituted with a substituent selected from Substituent Group A or Substituent Group B recited in [1], mono-5- to 10-membered heteroarylamino optionally substituted with a substituent selected from Substituent Group A or Substituent Group B recited in [1] or mono-4- to 10-membered non-aromatic heterocyclic amino optionally substituted with a substituent selected from Substituent Group A or Substituent Group B recited in [1].

[19] The pharmaceutical composition for treating esophageal cancer of any one of [1] to [17], wherein $R^9$ represents mono-$C_{3-10}$ cycloalkylamino optionally substituted with a substituent selected from Substituent Group A or Substituent Group B recited in [1] or mono-$C_{6-10}$ arylamino optionally substituted with a substituent selected from Substituent Group A or Substituent Group B recited in [1].

[19-1] The pharmaceutical composition for treating esophageal cancer of any one of [1] to [17], wherein $R^9$ represents mono-$C_{3-10}$ cycloalkylamino optionally substituted with a substituent selected from Substituent Group I or mono-$C_{6-10}$ arylamino optionally substituted with a substituent selected from Substituent Group I, wherein Substituent Group I consists of halogen, trifluoromethyl, cyano, $C_{1-6}$ alkyl and $C_{1-6}$ alkoxy.

[19-2] The pharmaceutical composition for treating esophageal cancer of any one of [1] to [17], wherein $R^9$ represents cyclopentylamino optionally substituted with a substituent selected from Substituent Group I recited in [19-1], cyclohexylamino optionally substituted with a substituent selected from Substituent Group I recited in [19-1], cycloheptylamino optionally substituted with a substituent selected from Substituent Group I recited in [19-1] or phenylamino optionally substituted with a substituent selected from Substituent Group I recited in [19-1].

[20] The pharmaceutical composition for treating esophageal cancer of [1], wherein the compound represented by the formula (I) is (1) N-[4-({2-[({4-[2-(Dimethylamino)ethyl]piperazin-1-yl}carbonyl)amino]pyridin-4-yl}oxy)-2-fluorophenyl]-N'-(4-fluorophenyl)cyclopropane-1,1-dicarboxamide, (2) N-(2-Fluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide, (3) N-(4-Fluorophenyl)-N'-{2-fluoro-4-[(2-{[(4-pyrrolidin-1-ylpiperidin-1-yl)carbonyl]amino}pyridin-4-yl)oxy]phenyl}cyclopropane-1,1-dicarboxamide, (4) N-[4-({2-[({4-[(Dimethylamino)methyl]piperidin-1-yl}carbonyl)amino]pyridin-4-yl}oxy)-2-fluorophenyl]-N'-(4-fluorophenyl)cyclopropane-1,1-dicarboxamide, (5) N-{4-[(2-{[(4-Azetidin-1-ylpiperidin-1-yl)carbonyl]amino}pyridin-4-yl)oxy]-2-fluorophenyl}-N'-(4-fluorophenyl)cyclopropane-1,1-dicarboxamide, (6) N-[4-({2-[({4-[3-(Dimethylamino)azetidin-1-yl]piperidin-1-yl}carbonyl)amino]pyridin-4-yl}oxy)-2-fluorophenyl]-N'-(4-fluorophenyl)cyclopropane-1,1-dicarboxamide, (7) N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide, (8) N-(2-Fluoro-4-{[2-({[4-(1-methylpiperidin-4-yl)piperazin-1-yl]carbonyl}amino)pyridin-4-yl]oxy}phenyl)-N'-(4-fluorophenyl)cyclopropane-1,1-dicarboxamide, (9) N-(2-Fluoro-4-{[2-({[4-(1-methylazetidin-3-yl)piperazin-1-yl]carbonyl}amino)pyridin-4-yl]oxy}phenyl)-N'-(4-fluorophenyl)cyclopropane-1,1-dicarboxamide,

(10) N-(4-{[2-({[4-(Dimethylamino)piperidin-1-yl]carbonyl}amino)pyridin-4-yl]oxy}-2-fluorophenyl)-N'-(4-fluorophenyl)cyclopropane-1,1-dicarboxamide,

(11) N-(4-{[2-({[4-(Azetidin-1-ylmethyl)piperidin-1-yl]carbonyl}amino)pyridin-4-yl]oxy}-2-fluorophenyl)-N'-(4-fluorophenyl)cyclopropane-1,1-dicarboxamide,

(12) N-(4-Fluorophenyl)-N'-(2-fluoro-4-{[2-({[4-(pyrrolidin-1-ylmethyl)piperidin-1-yl]carbonyl}amino)pyridin-4-yl]oxy}phenyl)cyclopropane-1,1-dicarboxamide,

(13) N-(4-{[2-({[(3S)-3-(Dimethylamino)pyrrolidin-1-yl]carbonyl}amino)pyridin-4-yl]oxy}-2-fluorophenyl)-N'-(4-fluorophenyl)cyclopropane-1,1-dicarboxamide,

(14) N-(4-{[2-({[(3R)-3-(Dimethylamino)pyrrolidin-1-yl]carbonyl}amino)pyridin-4-yl]oxy}-2-fluorophenyl)-N'-(4-fluorophenyl)cyclopropane-1,1-dicarboxamide,

(15) N-(2-Fluoro-4-{[2-({[methyl(1-methylpiperidin-4-yl)amino]carbonyl}amino)pyridin-4-yl]oxy}phenyl)-N'-phenylcyclopropane-1,1-dicarboxamide,

(16) N-(2-Fluoro-4-{[2-({[4-(4-methylpiperazin-1-yl)piperidin-1-yl]carbonyl}amino)pyridin-4-yl]oxy}phenyl)-N'-phenylcyclopropane-1,1-dicarboxamide,

(17) N-[4-({2-[({4-[3-(Dimethylamino)azetidin-1-yl]piperidin-1-yl}carbonyl)amino]pyridin-4-yl}oxy)-2-fluorophenyl]-N'-phenylcyclopropane-1,1-dicarboxamide,

(18) N-(4-{[2-({[(1-Ethylpiperidin-4-yl)(methyl)amino]carbonyl}amino)pyridin-4-yl]oxy}-2-fluorophenyl)-N'-phenylcyclopropane-1,1-dicarboxamide,

(19) N-[4-({2-[(Azetidin-1-ylcarbonyl)amino]pyridin-4-yl}oxy)-2-fluorophenyl]-N'-(4-fluorophenyl)cyclopropane-1,1-dicarboxamide,

(20) N-(4-Fluorophenyl)-N'-[2-fluoro-4-({2-[(pyrrolidin-1-ylcarbonyl)amino]pyridin-4-yl}oxy)phenyl]cyclopropane-1,1-dicarboxamide,

(21) N-{2-Fluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide,

(22) N-[4-({2-[(1,3'-Biazetidin-1'-ylcarbonyl)amino]pyridin-4-yl}oxy)-2-fluorophenyl]-N'-(4-fluorophenyl)cyclopropane-1,1-dicarboxamide,

(23) N-(2-Fluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide,

(24) N-(4-{[2-({[3-(Dimethylamino)azetidin-1-yl]carbonyl}amino)pyridin-4-yl]oxy}-2-fluorophenyl)-N'-(4-fluorophenyl)cyclopropane-1,1-dicarboxamide,

(25) N-[4-({2-[({3-[(Dimethylamino)methyl]azetidin-1-yl}carbonyl)amino]pyridin-4-yl}oxy)-2-fluorophenyl]-N'-(4-fluorophenyl)cyclopropane-1,1-dicarboxamide,

(26) N-{2-Fluoro-4-[(2-{[(4-hydroxypiperidin-1-yl)carbonyl]amino}pyridin-4-yl)oxy]phenyl}-N'-(4-fluorophenyl)cyclopropane-1,1-dicarboxamide,

(27) N-(2-Fluoro-4-{[2-({[4-(hydroxymethyl)piperidin-1-yl]carbonyl}amino)pyridin-4-yl]oxy}phenyl)-N'-(4-fluorophenyl)cyclopropane-1,1-dicarboxamide,

(28) N-(2-Fluoro-4-{[2-({[(3R)-3-hydroxypyrrolidin-1-yl]carbonyl}amino)pyridin-4-yl]oxy}phenyl)-N'-(4-fluorophenyl)cyclopropane-1,1-dicarboxamide,

(29) N-(2-Fluoro-4-{[2-({[(3S)-3-hydroxypyrrolidin-1-yl]carbonyl}amino)pyridin-4-yl]oxy}phenyl)-N'-(4-fluorophenyl)cyclopropane-1,1-dicarboxamide,

(30) N-[4-({2-[(Azetidin-1-ylcarbonyl)amino]pyridin-4-yl}oxy)-2,5-difluorophenyl]-N'-(4-fluorophenyl)cyclopropane-1,1-dicarboxamide,

(31) N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide,

(32) N-(2,5-Difluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide,

(33) N-[2,5-Difluoro-4-({2-[({3-[(dimethylamino)methyl]azetidin-1-yl}carbonyl)amino]pyridin-4-yl}oxy)phenyl]-N'-(4-fluorophenyl)cyclopropane-1,1-dicarboxamide,

(34) N-(2,5-Difluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide,

(35) N-{4-[(2-{[3-(Azetidin-1-ylmethyl)azetidin-1-ylcarbonyl]amino}pyridin-4-yl)oxy]-2,5-difluorophenyl}-N'-(4-fluorophenyl)cyclopropane-1,1-dicarboxamide,

(36) N-(2,5-Difluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide,

(37) N-{2,5-Difluoro-4-[(4-{[(3-hydroxyazetidin-1-yl)carbonyl]amino}pyrimidin-6-yl)oxy]phenyl}-N'-(4-fluorophenyl)cyclopropane-1,1-dicarboxamide,

(38) N-[4-({4-[({3-[(Dimethylamino)methyl]azetidin-1-yl}carbonyl)amino]pyrimidin-6-yl}oxy)-2,5-difluorophenyl]-N'-(4-fluorophenyl)cyclopropane-1,1-dicarboxamide,

(39) N-(2,5-Difluoro-4-{[4-({[3-(hydroxymethyl)azetidin-1-yl]carbonyl}amino)pyrimidin-6-yl]oxy}phenyl)-N'-(4-fluorophenyl)cyclopropane-1,1-dicarboxamide,

(40) N-(2,5-Difluoro-4-{[4-({[methyl(1-methylpiperidin-4-yl)amino]carbonyl}amino)pyrimidin-6-yl]oxy}phenyl)-N'-(4-fluorophenyl)cyclopropane-1,1-dicarboxamide,

(41) N-(2,5-Difluoro-4-{[4-({[4-(4-methylpiperazin-1-yl)piperidin-1-yl]carbonyl}amino)pyrimidin-6-yl]oxy}phenyl)-N'-(4-fluorophenyl)cyclopropane-1,1-dicarboxamide,

(42) N-(4-{[2-({[4-(Dimethylamino)piperidin-1-yl]carbonyl}amino)pyridin-4-yl]oxy}-2,5-difluorophenyl)-N'-(4-fluorophenyl)cyclopropane-1,1-dicarboxamide,

(43) N-{2,5-Difluoro-4-[(2-{[(4-methylpiperazin-1-yl)carbonyl]amino}pyridin-4-yl)oxy]phenyl}-N'-(4-fluorophenyl)cyclopropane-1,1-dicarboxamide,

(44) N-{2,5-Difluoro-4-[(2-{[(4-hydroxypiperidin-1-yl)carbonyl]amino}pyridin-4-yl)oxy]phenyl}-N'-(4-fluorophenyl)cyclopropane-1,1-dicarboxamide,

(45) N-{4-[(2-{[(4-Azetidin-1-ylpiperidin-1-yl)carbonyl]amino}pyridin-4-yl)oxy]oxy}-2,5-difluorophenyl}-N'-(4-fluorophenyl)cyclopropane-1,1-dicarboxamide,

(46) N-(2,5-Difluoro-4-{[2-({[3-(2-dimethylaminoacetoxy)azetidin-1-yl]carbonyl}amino)pyridin-4-yl]oxy}phenyl)-N'-(4-fluorophenyl)cyclopropane-1,1-dicarboxamide,
(47) N-(2,5-Difluoro-4-{[2-({[(3S)-3-hydroxypyrrolidin-1-yl]carbonyl}amino)pyridin-4-yl]oxy}phenyl)-N'-(4-fluorophenyl)cyclopropane-1,1-dicarboxamide or
(48) N-(2,5-Difluoro-4-{[2-({[(3R)-3-hydroxypyrrolidin-1-yl]carbonyl}amino)pyridin-4-yl]oxy}phenyl)-N'-(4-fluorophenyl)cyclopropane-1,1-dicarboxamide.

[21] The pharmaceutical composition for treating esophageal cancer of [1], wherein the compound represented by the formula (I) is
(1) N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide
(2) N-[4-({2-[(azetidin-1-ylcarbonyl)amino]pyridin-4-yl}oxy)-2-fluorophenyl]-N'-(4-fluorophenyl)cyclopropane-1,1-dicarboxamide
(3) N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide
(4) N-(2,5-Difluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide
(5) N-(2,5-Difluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide or
(6) N-(2,5-Difluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide.
[22] A method of treating esophageal cancer, comprising the step of administering to a patient suffering from esophageal cancer, the pharmaceutical composition for treating esophageal cancer of any one of [1] to [21]
[23] Use of the compound represented by the formula (I) above, the salt thereof or the hydrate of the foregoing for the preparation of a pharmaceutical composition for treating esophageal cancer.
[24] A compound represented by the formula (I) above, a salt thereof or a hydrate of the foregoing for use as a pharmaceutical composition for treating esophageal cancer.

Effect of the Invention

The compound of the present invention has inhibitory action against HGFR tyrosine kinase and inhibits proliferation of human cancer cells via HGFR activation as described in WO 2007/023768. The compound of the present invention also inhibits migration of human cancer cells. Furthermore, the compound of the present invention inhibits proliferation of vascular endothelial cells via HGF-HGFR signal.

The compound of the present invention inhibits proliferation of human esophageal cancer cells (Pharmacological Test Example 1). Therefore, the compound of the present invention is useful as a pharmaceutical composition for treating esophageal cancer.

However, the kind of cancers treated by the pharmaceutical composition for treating cancer or agent for treating cancer are not particularly limited, and include brain tumor (including pituitary adenoma and glioma), head and neck cancer, neck cancer, jaw cancer, maxillary cancer, submandibular gland cancer, mouth cancer (including tongue cancer, floor of mouth cancer, gum cancer, buccal mucosa cancer and hard palate cancer), salivary gland cancer, sublingual gland cancer, parotid gland cancer, nasal cavity cancer, paranasal sinus cancer (including maxillary sinus cancer, frontal sinus cancer, ethmoid sinus cancer and sphenoid sinus cancer), laryngeal cancer (including supraglottic cancer, glottis cancer and subglottic cancer), esophageal cancer, pulmonary cancer (including bronchogenic cancer, non-small-cell lung cancer (including lung adenocarcinoma, squamous cell carcinoma and large-cell lung cancer), small cell lung cancer (including oat cell carcinoma (lymphocyte-like type) and intermediate cell type, mixed small-cell and large cell lung cancer)), breast cancer, pancreatic cancer (including pancreatic ductal carcinoma), gastric cancer (including scirrhous gastric cancer and undifferentiated gastric cancer), biliary tract cancer (including cholangiocarcinoma and gallbladder cancer), small intestine or duodenum cancer, colorectal cancer (including colon cancer, rectal cancer, cecal cancerm, sigmoid colon cancer, ascending colon cancer, transverse colon cancer, descending colon cancer), bladder cancer, renal cancer (including renal cell carcinoma), hepatic cancer (including hepatocellular carcinoma, intrahepatic bile duct cancer), prostate cancer, uterine cancer (including cervical cancer, endometrial cancer), ovarian cancer, thyroid cancer, pharyngeal cancer (including nasopharyngeal carcinoma, oropharyngeal cancer, hypopharyngeal cancer), sarcoma (including osteosarcoma, chondrosarcoma, Kaposi's sarcoma, myosarcoma, angiosarcoma, fiber sarcoma), malignant lymphoma (including Hodgkin's lymphoma, non-Hodgkin's lymphoma), leukemia (including chronic myelogenous leukemia (CML), acute myeloid leukemia (AML), chronic lymphoblastic leukemia (CLL) and acute lymphoblastic leukemia (ALL), including such as lymphoma, multiple myeloma (MM), myelodysplastic-myeloproliferative disease), skin cancer (including basal cell carcinoma, squamous cell carcinoma, malignant melanoma, mycosis fungoides, Sezary syndrome, actinic keratosis, Bowen's disease, Paget's disease), and melanoma.

DESCRIPTION OF THE PREFERRED EMBODIMENTS

The symbols and terms as used herein will be defined and the present invention will be described in details below.

Several of the structural formulas for the compounds throughout the present specification represent only one isomeric form for convenience, but the invention encompasses any and all of the geometric isomers as well as optical isomers based on asymmetric carbons, stereoisomers and tautomers, and mixtures of those isomers, which are implied by the structures of the compounds, without being limited to any of the formulas shown for convenience. The compounds of the invention therefore include all those having asymmetric carbons therein and existing in optically active or racemic form, with no particular restrictions on the invention. There are also no restrictions when polymorphic crystalline forms thereof exist, and the compounds may be in one crystalline form or a mixture of different crystalline forms, while anhydrates and hydrates of the compounds of the invention are also included.

The so-called metabolite, a compound which a compound according to the present invention is metabolized in a living body through oxidation, reduction, hydrolysis, conjugation and the others to provide, and the so-called prodrug, a compound which is metabolized in a living body through oxidation, reduction, hydrolysis, conjugation and the others to provide a compound according to the present invention, are also included within the claimed scope of the present invention.

The "salt" includes a salt of an inorganic acid, a salt of an organic acid, a salt of an inorganic base, a salt of an organic base and a salt of an acidic or basic amino acid, among them, a pharmacologically acceptable salt is preferable.

The preferable salt of an inorganic acid includes, for example, a salt of hydrochloric acid, hydrobromic acid, sulfuric acid, nitric acid and phosphoric acid. The preferable salt of an organic acid includes, for example, a salt of acetic acid, succinic acid, fumaric acid, maleic acid, tartaric acid, citric acid, lactic acid, stearic acid, benzoic acid, methanesulfonic acid, ethanesulfonic acid, and p-toluenesulfonic acid.

The preferable salt of an inorganic base includes, for example, an alkali metal salt such as sodium salt and potassium salt, an alkali earth metal salt such as calcium salt and magnesium salt, aluminum salt, and ammonium salt. The preferable salt of an organic base includes, for example, a salt of diethylamine, diethanolamine, meglumine, and N,N-dibenzylethylenediamine.

The preferable salt of an acidic amino acid includes, for example, a salt of aspartic acid and glutamic acid. The preferable salt of a basic amino acid includes, for example, a salt of arginine, lysine and ornithine.

The "halogen" represents fluorine, chlorine, bromine or iodine.

The "$C_{1-6}$ alkyl" represents an alkyl of straight or branched chain having a carbon number of 1 to 6, and includes, for specific example, methyl, ethyl, 1-propyl (n-propyl), 2-propyl (i-propyl), 2-methyl-1-propyl (i-butyl), 2-methyl-2-propyl (t-butyl), 1-butyl (n-butyl), 2-butyl (s-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl, and 2,3-dimethyl-2-butyl.

The "$C_{2-6}$ alkenyl" represents an alkenyl of straight or branched chain having one double bond and a carbon number of 2 to 6, and includes, for specific example, ethenyl (vinyl), 1-propenyl, 2-propenyl (allyl), 1-butenyl, 2-butenyl, 3-butenyl, pentenyl, and hexenyl.

The "$C_{3-6}$ alkenyl" represents an alkenyl of straight or branched chain having one double bond and a carbon number of 3 to 6, and includes, for specific example, 2-propenyl (allyl), 2-butenyl, 3-butenyl, pentenyl, and hexenyl.

The "$C_{2-6}$ alkynyl" represents an alkynyl of straight or branched chain having one triple bond and a carbon number of 2 to 6, and includes, for specific example, ethynyl, 1-propynyl, 2-propynyl, 1-butynyl, 2-butynyl, 3-butynyl, pentynyl, and hexynyl.

The "$C_{3-6}$ alkynyl" represents an alkynyl of straight or branched chain having one triple bond and a carbon number of 3 to 6, and includes, for specific example, 2-propynyl, 2-butynyl, 3-butynyl, pentynyl, and hexynyl.

The "$C_{1-6}$ alkylene" represents a divalent group derived by eliminating further any one hydrogen from the "$C_{1-6}$ alkyl" defined above, and includes, for specific example, methylene, 1,2-ethylene, 1,1-ethylene, 1,3-propylene, tetramethylene, pentamethylene, and hexamethylene.

The "$C_{3-10}$ cycloalkyl" represents a mono- or di-cyclic saturated aliphatic hydrocarbon group having a carbon number of 3 to 10, and includes, for specific example, cyclopropyl, cyclobutyl, cyclopentyl, cyclohexyl, cycloheptyl, cyclooctyl, cyclononyl, cyclodecyl, bicyclo[2.1.0]pentyl, bicyclo[3.1.0]hexyl, bicyclo[2.1.1]hexyl, bicyclo[4.1.0]heptyl, bicyclo[2.2.1]heptyl (norbornyl), bicyclo[3.3.0]octyl, bicyclo[3.2.1]octyl, bicyclo[2.2.2]octyl, bicyclo[4.3.0]nonyl, bicyclo[3.3.1]nonyl, bicyclo[4.4.0]decyl (decalyl), and bicyclo[3.3.2]decyl.

The "$C_{6-10}$ aryl" represents an aromatic hydrocarbon ring group having a carbon number of 6 to 10, and includes, for specific example, phenyl, 1-naphthyl, 2-naphthyl, indenyl, azulenyl, and heptalenyl.

The "heteroatom" represents nitrogen, oxygen, or sulfur.

The "5- to 10-membered heteroaryl" represents an aromatic ring group having 5 to 10 atoms forming the ring and containing 1 to 5 heteroatoms, and includes, for specific example, furyl, thienyl, pyrrolyl, imidazolyl, triazolyl, tetrazolyl, thiazolyl, pyrazolyl, oxazolyl, isoxazolyl, isothiazolyl, furazanyl, thiadiazolyl, oxadiazolyl, pyridyl, pyrazinyl, pyridazinyl, pyrimidinyl, triazinyl, purinyl, pteridinyl, quinolyl, isoquinolyl, naphthylidinyl, quinoxalinyl, cinnolinyl, quinazolinyl, phthalazinyl, imidazopyridyl, imidazothiazolyl, imidazoxazolyl, benzothiazolyl, benzoxazolyl, benzimidazolyl, indolyl, isoindolyl, indazolyl, pyrrolopyridyl, thienopyridyl, furopyridyl, benzothiadiazolyl, benzoxadiazolyl, pyridopyrimidinyl, benzofuryl, benzothienyl, and thienofuryl.

The preferable example of the "5- to 10-membered heteroaryl" includes furyl, thienyl, pyrrolyl, imidazolyl, thiazolyl, pyrazolyl, oxazolyl, isoxazolyl, isothiazolyl, pyridyl, and pyrimidinyl.

The "3- to 10-membered non-aromatic heterocyclic group" represents
(1) a monocyclic or a bicyclic non-aromatic heterocyclic group
(2) having 3 to 10 atoms in the ring,
(3) containing 1 to 2 heteroatoms among the atoms of the ring,
(4) optionally containing 1 to 2 double bonds in the ring,
(5) optionally containing 1 to 3 carbonyl, sulfinyl, or sulfonyl in the ring.

If the group contains nitrogen in the ring, the nitrogen may have a bond not participating in the formation of the ring. The group includes, for specific example, aziridinyl, azetidinyl, pyrrolidinyl, piperidinyl, azepanyl, azocanyl, piperazinyl, diazepanyl, diazocanyl, diazabicyclo[2.2.1]heptyl, morpholinyl, thiomorpholinyl, 1,1-dioxothiomorpholinyl, oxiranyl, oxetanyl, tetrahydrofuryl, tetrahydropyranyl, dioxanyl, tetrahydrothienyl, tetrahydrothiopyranyl, oxazolidinyl, and thiazolidinyl.

The preferable example of the "3- to 10-membered non-aromatic heterocyclic group" includes aziridinyl, azetidinyl, pyrrolidinyl, piperidinyl, azepanyl, piperazinyl, diazepanyl, morpholinyl, thiomorpholinyl, 1,1-dioxothiomorpholinyl, tetrahydrofuryl, and tetrahydropyranyl.

The "4- to 10-membered non-aromatic heterocyclic group" represents
(1) a monocyclic or a bicyclic non-aromatic heterocyclic group
(2) having 4 to 10 atoms in the ring,
(3) containing 1 to 2 heteroatoms among the atoms of the ring,
(4) optionally containing 1 to 2 double bonds in the ring,
(5) optionally containing 1 to 3 carbonyl, sulfinyl, or sulfonyl in the ring.

If the group contains nitrogen in the ring, the nitrogen may have a bond not participating in the formation of the ring. The group includes, for specific example, azetidinyl, pyrrolidinyl, piperidinyl, azepanyl, azocanyl, piperazinyl, diazepanyl, diazocanyl, diazabicyclo[2.2.1]heptyl, morpholinyl, thiomorpholinyl, 1,1-dioxothiomorpholinyl, oxetanyl, tetrahydrofuryl, tetrahydropyranyl, dioxanyl, tetrahydrothienyl, tetrahydrothiopyranyl, oxazolidinyl, and thiazolidinyl.

The preferable example of the "4- to 10-membered non-aromatic heterocyclic group" includes azetidinyl, pyrrolidinyl, piperidinyl, azepanyl, piperazinyl, diazepanyl, morpholinyl, thiomorpholinyl, 1,1-dioxothiomorpholinyl, tetrahydrofuryl, and tetrahydropyranyl.

The "$C_{3-10}$ cycloalkyl-$C_{1-6}$ alkyl" represents a group obtained by substituting any one hydrogen of the above defined "$C_{1-6}$ alkyl" with the above defined "$C_{3-10}$ cycloalkyl", and includes, for specific example, cyclopropylmethyl, cyclobutylmethyl, cyclopentylmethyl, cyclohexylmethyl, cycloheptylmethyl, cyclooctylmethyl, cyclononylmethyl, cyclodecylmethyl, bicyclo[2.2.1]heptylmethyl (norbornylmethyl), and bicyclo[4.4.0]decylmethyl (decarylmethyl).

The "$C_{6-10}$ aryl-$C_{1-6}$ alkyl" represents a group obtained by substituting any one hydrogen of the above defined "$C_{1-6}$ alkyl" with the above defined "$C_{6-10}$ aryl", and includes, for specific example, benzyl, 1-naphthylmethyl, 2-naphthylmethyl, phenethyl, 1-naphthylethyl, and 2-naphthylethyl.

The "5- to 10-membered heteroaryl-$C_{1-6}$ alkyl" represents a group obtained by substituting any one hydrogen of the above defined "$C_{1-6}$ alkyl" with the above defined "5- to 10-membered heteroaryl", and includes, for specific example, furylmethyl, thienylmethyl, pyrrolylmethyl, imidazolylmethyl, triazolylmethyl, tetrazolylmethyl, thiazolylmethyl, pyrazolylmethyl, oxazolylmethyl, isoxazolylmethyl, isothiazolylmethyl, furazanylmethyl, thiadiazolylmethyl, oxadiazolylmethyl, pyridylmethyl, pyrazinylmethyl, pyridazinylmethyl, pyrimidinylmethyl, triazinylmethyl, furyl ethyl, thienylethyl, pyrrolylethyl, imidazolyl ethyl, triazolylethyl, tetrazolylethyl, thiazolylethyl, pyrazolylethyl, oxazolylethyl, isoxazolylethyl, isothiazolylethyl, furazanylethyl, thiadiazolylethyl, oxadiazolylethyl, pyridylethyl, pyrazinylethyl, pyridazinylethyl, pyrimidinylethyl, and triazinylethyl.

The preferable example of the "5- to 10-membered heteroaryl $C_{1-6}$ alkyl" includes furylmethyl, thienylmethyl, pyrrolylmethyl, imidazolylmethyl, thiazolylmethyl, pyrazolylmethyl, oxazolylmethyl, isoxazolylmethyl, isothiazolylmethyl, pyridylmethyl, pyrimidinylmethyl, furylethyl, thienylethyl, pyrrolylethyl, imidazolylethyl, thiazolylethyl, pyrazolylethyl, oxazolylethyl, isoxazolylethyl, isothiazolylethyl, pyridylethyl, and pyrimidinylethyl.

The "3- to 10-membered non-aromatic heterocyclic-$C_{1-6}$ alkyl" represents a group obtained by substituting any one hydrogen of the above defined "$C_{1-6}$ alkyl" with the above defined "3- to 10-membered heterocyclic group", and includes, for specific example, aziridinylmethyl, azetidinylmethyl, pyrrolidinylmethyl, piperidinylmethyl, azepanylmethyl, azocanylmethyl, piperazinylmethyl, diazepanylmethyl, diazocanylmethyl, morpholinylmethyl, thiomorpholinylmethyl, 1,1-dioxothiomorpholinylmethyl, oxiranylmethyl, oxetanylmethyl, tetrahydrofurylmethyl, tetrahydropyranylmethyl, dioxanylmethyl, tetrahydrothienylmethyl, tetrahydrothiopyranylmethyl, oxazolidinylmethyl, thiazolidinylmethyl, aziridinylethyl, azetidinylethyl, pyrrolidinylethyl, piperidinylethyl, azepanylethyl, azocanylethyl, piperazinylethyl, diazepanylethyl, diazocanylethyl, morpholinylethyl, thiomorpholinylethyl, 1,1-dioxothiomorpholinylethyl, oxiranylethyl, oxetanyl ethyl, tetrahydrofuryl ethyl, tetrahydropyranylethyl, dioxanylethyl, tetrahydrothienylethyl, tetrahydrothiopyranylethyl, oxazolidinylethyl, and thiazolidinylethyl.

The preferable example of the "3- to 10-membered non-aromatic heterocyclic-$C_{1-6}$ alkyl" includes azetidinylmethyl, pyrrolidinylmethyl, piperidinylmethyl, azepanylmethyl, piperazinylmethyl, diazepanylmethyl, morpholinylmethyl, thiomorpholinylmethyl, tetrahydrofurylmethyl, azetidinylethyl, pyrrolidinylethyl, piperidinylethyl, azepanylethyl, piperazinylethyl, diazepanylethyl, morpholinylethyl, thiomorpholinylethyl, and tetrahydrofurylethyl.

The "$C_{1-6}$ alkoxy" represents a group obtained by adding oxygen to the terminal of the above defined "$C_{1-6}$ alkyl", and includes, for specific example, methoxy, ethoxy, 1-propoxy (n-propoxy), 2-propoxy (i-propoxy), 2-methyl-1-propoxy (i-butoxy), 2-methyl-2-propoxy (t-butoxy), 1-butoxy (n-butoxy), 2-butoxy (s-butoxy), 1-pentyloxy, 2-pentyloxy, 3-pentyloxy, 2-methyl-1-butoxy, 3-methyl-1-butoxy, 2-methyl-2-butoxy, 3-methyl-2-butoxy, 2,2-dimethyl-1-propoxy, 1-hexyloxy, 2-hexyloxy, 3-hexyloxy, 2-methyl-1-pentyloxy, 3-methyl-1-pentyloxy, 4-methyl-1-pentyloxy, 2-methyl-2-pentyloxy, 3-methyl-2-pentyloxy, 4-methyl-2-pentyloxy, 2-methyl-3-pentyloxy, 3-methyl-3-pentyloxy, 2,3-dimethyl-1-butoxy, 3,3-dimethyl-1-butoxy, 2,2-dimethyl-1-butoxy, 2-ethyl-1-butoxy, 3,3-dimethyl-2-butoxy, and 2,3-dimethyl-2-butoxy.

The "$C_{1-6}$ alkylthio" represents a group obtained by adding sulfur to the terminal of the above defined "$C_{1-6}$ alkyl", and includes, for specific example, methylthio, ethylthio, 1-propylthio (n-propylthio), 2-propylthio (i-propylthio), 2-methyl-1-propylthio (i-butylthio), 2-methyl-2-propylthio (t-butylthio), 1-butylthio (n-butylthio), 2-butylthio (s-butylthio), 1-pentylthio, 2-pentylthio, 3-pentylthio, 2-methyl-1-butylthio, 3-methyl-1-butylthio, 2-methyl-2-butylthio, 3-methyl-2-butylthio, 2,2-dimethyl-1-propylthio, 1-hexylthio, 2-hexylthio, 3-hexylthio, 2-methyl-1-pentylthio, 3-methyl-1-pentylthio, 4-methyl-1-pentylthio, 2-methyl-2-pentylthio, 3-methyl-2-pentylthio, 4-methyl-2-pentylthio, 2-methyl-3-pentylthio, 3-methyl-3-pentylthio, 2,3-dimethyl-1-butylthio, 3,3-dimethyl-1-butylthio, 2,2-dimethyl-1-butylthio, 2-ethyl-1-butylthio, 3,3-dimethyl-2-butylthio, and 2,3-dimethyl-2-butylthio.

The "$C_{3-6}$ alkenyloxy" represents a group obtained by adding oxygen to the terminal of the above defined "$C_{3-6}$ alkenyl", and includes, for specific example, 2-propenyloxy (allyloxy), 2-butenyloxy, 3-butenyloxy, pentenyloxy, and hexenyloxy.

The "$C_{3-6}$ alkenylthio" represents a group obtained by adding sulfur to the terminal of the above defined "$C_{3-6}$ alkenyl", and includes, for specific example, 2-propenylthio (allylthio), 2-butenylthio, 3-butenylthio, pentenylthio, and hexenylthio.

The "$C_{3-6}$ alkynyloxy" represents a group obtained by adding oxygen to the terminal of the above defined "$C_{3-6}$ alkynyl", and includes, for specific example, 2-propynyloxy, 2-butynyloxy, 3-butynyloxy, pentynyloxy, and hexynyloxy.

The "$C_{3-6}$ alkynylthio" represents a group obtained by adding sulfur to the terminal of the above defined "$C_{3-6}$ alkynyl", and includes, for specific example, 2-propynylthio, 2-butynylthio, 3-butynylthio, pentynylthio, and hexynylthio.

The "$C_{3-10}$ cycloalkoxy" represents a group obtained by adding oxygen to the terminal of the above defined "$C_{3-10}$ cycloalkyl", and includes, for specific example, cyclopropoxy, cyclobutoxy, cyclopentyloxy, cyclohexyloxy, cycloheptyloxy, and cyclooctyloxy.

The "$C_{3-10}$ cycloalkylthio" represents a group obtained by adding sulfur to the terminal of the above defined "$C_{3-10}$ cycloalkyl", and includes, for specific example, cyclopropylthio, cyclobutylthio, cyclopentylthio, cyclohexylthio, cycloheptylthio, and cyclooctylthio.

The "$C_{6-10}$ aryloxy" represents a group obtained by adding oxygen to the terminal of the above defined "$C_{6-10}$ aryl", and includes, for specific example, phenoxy, 1-naphthoxy, 2-naphthoxy, indenyloxy, azulenyloxy, and heptalenyloxy.

The "$C_{6-10}$ arylthio" represents a group obtained by adding sulfur to the terminal of the above defined "$C_{6-10}$ aryl", and includes, for specific example, phenylthio, 1-naphthylthio, 2-naphthylthio, indenylthio, azulenylthio, and heptalenylthio.

The "5- to 10-membered heteroaryloxy" represents a group obtained by adding oxygen to the terminal of the above defined "5- to 10-membered heteroaryl", and includes, for specific example, furyloxy, thienyloxy, pyrrolyloxy, imidazolyloxy, triazolyloxy, thiazolyloxy, pyrazolyloxy, oxazolyloxy, isoxazolyloxy, isothiazolyloxy, furazanyloxy, thiadiazolyloxy, oxadiazolyloxy, pyridyloxy, pyrazinyloxy, pyridazinyloxy, pyrimidinyloxy, and triazinyloxy.

The "5- to 10-membered heteroarylthio" represents a group obtained by adding sulfur to the terminal of the above defined "5- to 10-membered heteroaryl", and includes, for specific example, furylthio, thienylthio, pyrrolylthio, imidazolylthio, triazolylthio, thiazolylthio, pyrazolylthio, oxazolylthio, isoxazolylthio, isothiazolylthio, furazanylthio, thiadiazolylthio, oxadiazolylthio, pyridylthio, pyrazinylthio, pyridazinylthio, pyrimidinylthio, and triazinylthio.

The "4- to 10-membered non-aromatic heterocyclicoxy group" represents a group obtained by adding oxygen to the terminal of the above defined "4- to 10-membered non-aromatic heterocyclic group", and includes, for specific example, azetidinyloxy, pyrrolidinyloxy, piperidinyloxy, azepanyloxy, azocanyloxy, piperazinyloxy, diazepanyloxy, diazocanyloxy, morpholinyloxy, thiomorpholinyloxy, 1,1-dioxothiomorpholinyloxy, oxetanyloxy, tetrahydrofuryloxy, tetrahydropyranyloxy, tetrahydrothienyloxy, and tetrahydrothiopyranyloxy.

The "4- to 10-membered non-aromatic heterocyclicthio group" represents a group obtained by adding sulfur to the terminal of the above defined "4- to 10-membered non-aromatic heterocyclic group", and includes, for specific example, azetidinylthio, pyrrolidinylthio, piperidinylthio, azepanylthio, azocanylthio, piperazinylthio, diazepanylthio, diazocanylthio, oxetanylthio, tetrahydrofurylthio, tetrahydropyranylthio, tetrahydrothienylthio, and tetrahydrothiopyranylthio.

The "mono-$C_{1-6}$ alkylamino" represents a group obtained by substituting one hydrogen of amino with the above defined "$C_{1-6}$ alkyl", and includes, for specific example, methylamino, ethylamino, 1-propylamino (n-propylamino), 2-propylamino (i-propylamino), 2-methyl-1-propylamino (i-butylamino), 2-methyl-2-propylamino (t-butylamino), 1-butylamino (n-butylamino), 2-butylamino (s-butylamino), 1-pentylamino, 2-pentylamino, 3-pentylamino, 2-methyl-1-butylamino, 3-methyl-1-butylamino, 2-methyl-2-butylamino, 3-methyl-2-butylamino, 2,2-dimethyl-1-propylamino, 1-hexylamino, 2-hexylamino, 3-hexylamino, 2-methyl-1-pentylamino, 3-methyl-1-pentylamino, 4-methyl-1-pentylamino, 2-methyl-2-pentylamino, 3-methyl-2-pentylamino, 4-methyl-2-pentylamino, 2-methyl-3-pentylamino, 3-methyl-3-pentylamino, 2,3-dimethyl-1-butylamino, 3,3-dimethyl-1-butylamino, 2,2-dimethyl-1-butylamino, 2-ethyl-1-butylamino, 3,3-dimethyl-2-butylamino, and 2,3-dimethyl-2-butylamino.

The "mono-$C_{3-10}$ cycloalkylamino" represents a group obtained by substituting one hydrogen of amino with the above defined "$C_{3-10}$ cycloalkyl", and includes, for specific example, cyclopropylamino, cyclobutylamino, cyclopentylamino, cyclohexylamino, cycloheptylamino, and cyclooctylamino.

The "mono-$C_{6-10}$ arylamino" represents a group obtained by substituting one hydrogen of amino with the above defined "$C_{6-10}$ aryl", and includes, for specific example, phenylamino, 1-naphthylamino, 2-naphthylamino, indenylamino, azulenylamino, and heptalenylamino.

The "mono-5- to 10-membered heteroarylamino" represents a group obtained by substituting one hydrogen of amino with the above defined "5- to 10-membered heteroaryl", and includes, for specific example, furylamino, thienylamino, pyrrolylamino, imidazolylamino, triazolylamino, tetrazolylamino, thiazolylamino, pyrazolylamino, oxazolylamino, isoxazolylamino, isothiazolylamino, furazanylamino, thiadiazolylamino, oxadiazolylamino, pyridylamino, pyrazinylamino, pyridazinylamino, pyrimidinylamino, and triazinylamino.

The preferable example of the "mono-5- to 10-membered heteroarylamino" includes furylamino, thienylamino, pyrrolylamino, imidazolylamino, thiazolylamino, pyrazolylamino, oxazolylamino, isoxazolylamino, isothiazolylamino, pyridylamino, and pyrimidinylamino.

The "mono-4- to 10-membered non-aromatic heterocyclic amino" represents a group obtained by substituting one hydrogen of amino with the above defined "4- to 10-membered non-aromatic heterocyclic group", and includes, for specific example, azetidinylamino, pyrrolidinylamino, piperidinylamino, azepanylamino, azocanylamino, piperazinylamino, diazepanylamino, diazocanylamino, morpholinylamino, thiomorpholinylamino, 1,1-dioxothiomorpholinylamino, oxetanylamino, tetrahydrofurylamino, tetrahydropyranylamino, tetrahydrothienylamino, and tetrahydrothiopyranylamino.

The preferable example of the "mono-4- to 10-membered non-aromatic heterocyclic amino" includes pyrrolidinylamino, piperidinylamino, azepanylamino, piperazinylamino, diazepanylamino, morpholinylamino, thiomorpholinylamino, and tetrahydrofurylamino.

The "di-$C_{1-6}$ alkylamino" represents a group obtained by substituting two hydrogen of amino with the same or different groups of the above defined "$C_{1-6}$ alkyl", and includes, for specific example, N,N-dimethylamino, N,N-diethylamino, N,N-di-n-propylamino, N,N-di-i-propylamino, N,N-di-n-butylamino, N,N-di-i-butylamino, N,N-di-s-butylamino, N,N-di-t-butylamino, N-ethyl-N-methylamino, N-n-propyl-N-methylamino, N-i-propyl-N-methylamino, N-n-butyl-N-methylamino, N-i-butyl-N-methylamino, N-s-butyl-N-methylamino, and N-t-butyl-N-methylamino.

Each of the substituents in the compound of the present invention represented by the above formula (I) will be described below.

(Meaning of $R^1$)

$R^1$ represents a 3- to 10-membered non-aromatic heterocyclic group wherein the group is limited to a group having nitrogen as a ring constituent atom and the nitrogen having a bonding hand, or a group represented by the formula —$NR^{11a}R^{11b}$, wherein $R^{11a}$ and $R^{11b}$ may be the same or different and each represents hydrogen, $C_{1-6}$ alkyl, $C_{3-6}$ alkenyl, $C_{3-6}$ alkynyl, $C_{3-10}$ cycloalkyl, $C_{6-10}$-aryl, 5- to 10-membered heteroaryl or a 4- to 10-membered non-aromatic heterocyclic group, and $R^{11a}$ and $R^{11b}$ may be substituted with a substituent selected from Substituent Group A or Substituent Group B.

$R^1$ may be substituted with a substituent selected from Substituent Group A or Substituent Group B.

The preferable example of $R^1$ includes a group represented by the formula (II):

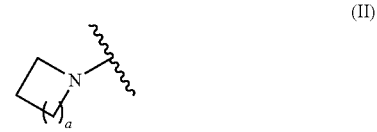

wherein a represents an integer of 1 to 4;
a group represented by the formula (III):

wherein b represents an integer of 1 to 3, and Z represents oxygen, sulfur, carbonyl, sulfonyl, or a group represented by the formula —$NR^Z$—, wherein $R^Z$ represents hydrogen or $C_{1-6}$ alkyl, and the groups represented by the formula (II) or (III) may be substituted with a substituent selected from Substituent Group A or Substituent Group B; or
a group represented by the formula —$NR^{11c}R^{11d}$, wherein $R^{11c}$ represents hydrogen or $C_{1-6}$ alkyl, and $R^{11d}$ represents $C_{1-6}$ alkyl or a group represented by the formula (IV):

wherein c represents an integer of 1 to 3, and $Z^1$ represents oxygen, sulfur, carbonyl, sulfonyl or a group represented by the formula —$NR^{Z1}$—, wherein $R^{Z1}$ represents hydrogen or $C_{1-6}$ alkyl, and $R^{11d}$ may be substituted with a substituent selected from Substituent Group A or Substituent Group B.

The more preferable example of $R^1$ includes azetidin-1-yl, pyrrolidin-1-yl, piperidin-1-yl, azepan-1-yl, piperazin-1-yl, diazepan-1-yl, morpholin-4-yl, thiomorpholin-4-yl, 1,1-dioxothiomorpholin-4-yl, or a group represented by the formula —$NR^{11e}R^{11f}$ wherein $R^{11e}$ represents hydrogen or $C_{1-6}$ alkyl, $R^{11f}$ represents $C_{1-6}$ alkyl, pyrrolidin-3-yl, piperidin-3-yl, piperidin-4-yl or tetrahydropyran-4-yl, and $R^{11f}$ may be substituted with a substituent selected from Substituent Group D, and each of the above substituents may be substituted with a substituent selected from Substituent Group D.

The even more preferable example of $R^1$ includes azetidin-1-yl, pyrrolidin-1-yl, piperidin-1-yl, piperazin-1-yl, diazepan-1-yl, morpholin-4-yl, and each of the above substituents may be substituted with a substituent selected from Substituent Group E, or a group represented by the formula —$NR^{11g}R^{11h}$ wherein $R^{11g}$ represents hydrogen or methyl, $R^{11h}$ represents n-propyl, n-butyl, pyrrolidin-3-yl, piperidin-3-yl, piperidin-4-yl or tetrahydropyran-4-yl, and $R^{11h}$ may be substituted with a substituent selected from Substituent Group F.

The especially preferable example of $R^1$ includes azetidin-1-yl, pyrrolidin-1-yl, piperidin-1-yl or piperazin-1-yl, wherein azetidin-1-yl may be substituted with a substituent selected from Substituent Group G and pyrrolidin-1-yl, piperidin-1-yl and piperazin-1-yl are substituted with a substituent selected from Substituent Group G, or a group represented by the formula —$N(CH_3)R^{11i}$ wherein $R^{11i}$ represents n-propyl, n-butyl, pyrrolidin-3-yl or piperidin-4-yl, and $R^{11i}$ is substituted with a substituent selected from Substituent Group H.

The most preferable example of $R^1$ includes azetidin-1-yl, pyrrolidin-1-yl, piperidin-1-yl or piperazin-1-yl, wherein azetidin-1-yl may be substituted with a substituent selected from Substituent Group G-1 and pyrrolidin-1-yl, piperidin-1-yl and piperazin-1-yl are substituted with a substituent selected from Substituent Group G-1, or azetidin-1-yl having dimethylamino, pyrrolidin-1-yl having dimethylamino or piperidin-1-yl having dimethylamino, a group represented by the formula —$N(CH_3)R^{11j}$ wherein $R^{11j}$ represents 1-methylpiperidin-4-yl or 1-ethylpiperidin-4-yl, azetidin-1-yl optionally substituted with a substituent selected from Substituent Group G-2, pyrrolidin-1-yl substituted with a substituent selected from Substituent Group G-2, piperidin-1-yl substituted with a substituent selected from Substituent Group G-2 or a group represented by the formula —$N(CH_3)R^{11k}$, wherein $R^{11k}$ represents 3-(dimethylamino)propyl or 1-[2-(dimethylamino)ethyl]piperidin-4-yl.

The most preferable example of $R^1$ also includes [2-(dimethylamino)ethyl]piperazin-1-yl, 4-pyrrolidin-1-ylpiperidin-1-yl, 4-[(dimethylamino)methyl]piperidin-1-yl, 4-azetidin-1-ylpiperidin-1-yl, 4-[3-(dimethylamino)azetidin-1-yl]piperidin-1-yl, 4-(4-methylpiperazin-1-yl)piperidin-1-yl, 4-(1-methylpiperidin-4-yl)piperazin-1-yl, 4-(1-methylazetidin-3-yl)piperazin-1-yl, 4-(dimethylamino)piperidin-1-yl, 4-(azetidin-1-ylmethyl)piperidin-1-yl, 4-(pyrrolidin-1-ylmethyl)piperidin-1-yl, (3S)-3-(dimethylamino)pyrrolidin-1-yl, (3R)-3-(dimethylamino)pyrrolidin-1-yl, azetidin-1-yl, pyrrolidin-1-yl, morpholin-4-yl, 4-methylpiperazin-1-yl, 3-hydroxyazetidin-1-yl, 1,3'-biazetidin-1'-yl, 3-(hydroxymethyl)azetidin-1-yl, 3-(dimethylamino)azetidin-1-yl, 3-[(dimethylamino)methyl]azetidin-1-yl, 4-hydroxypiperidin-1-yl, 4-(hydroxymethyl)piperidin-1-yl, (3R)-3-hydroxypyrrolidin-1-yl, (3S)-3-hydroxypyrrolidin-1-yl, 3-(azetidin-1-ylmethyl)azetidin-1-yl, 3-(2-dimethylaminoacetoxy)azetidin-1-yl, methyl(1-methylpiperidin-4-yl)amino, (1-ethylpiperidin-4-yl)(methyl)amino, [3-(dimethylamino)propyl](methyl)amino or {1-[2-(dimethylamino)ethyl]piperidin-4-yl}(methyl)amino.

(Meaning of Substituent Group A)
The Substituent Group A represents a group consisting of halogen, hydroxyl, mercapto, nitro, cyano and oxo.

(Meaning of Substituent Group B)
The Substituent Group B represents a group consisting of $C_{1-6}$ alkyl, $C_{2-6}$ alkenyl, $C_{2-6}$ alkynyl, $C_{3-10}$ cycloalkyl, $C_{6-10}$-aryl, 5- to 10-membered heteroaryl, a 3- to 10-membered non-aromatic heterocyclic group, $C_{1-6}$ alkoxy, $C_{3-6}$ alkenyloxy, $C_{3-6}$ alkynyloxy, $C_{3-10}$ cycloalkoxy, $C_{6-10}$ aryloxy, 5- to 10-membered heteroaryloxy, 4- to 10-membered non-aromatic heterocyclicoxy, $C_{1-6}$ alkylthio, $C_{3-6}$ alkenylthio, $C_{3-6}$ alkynylthio, $C_{3-10}$ cycloalkylthio, $C_{6-10}$ arylthio, 5- to 10-membered heteroarylthio, 4- to 10-membered non-aromatic heterocyclicthio, and a group represented by the formula -$T^1$-$T^2$-$T^3$, wherein $T^1$ represents a direct bond or $C_{1-6}$ alkylene, $T^2$ represents carbonyl, sulfinyl, sulfonyl, a group represented by the formula —C(=O)—O—, a group represented by the formula —O—C(=O)—, a group represented by the formula —$SO_2$—O—, a group represented by the formula —O—$SO_2$—, a group represented by the formula —$NR^{T1}$—, a group represented by the formula —C(=O)—$NR^{T1}$—, a group represented by the formula —$NR^{T1}$—C(=O)—, a group represented by the formula —$SO_2$—$NR^{T1}$— or a group represented by the formula —$NR^{T1}$—$SO_2$—, $T^3$ represents hydrogen, $C_{1-6}$ alkyl, $C_{3-6}$ alkenyl, $C_{3-6}$ alkynyl, $C_{3-10}$ cycloalkyl, $C_{6-10}$ aryl, 5- to 10-membered heteroaryl or a 4- to 10-membered non-aromatic heterocyclic group, and $R^{T1}$ represents hydrogen or $C_{1-6}$ alkyl.

Each group included in Substituent Group B may be substituted with a substituent selected from Substituent Group C.

(Meaning of Substituent Group C)
The Substituent Group C represents a group consisting of halogen, hydroxyl, mercapto, nitro, cyano, oxo, $C_{1-6}$ alkyl, $C_{2-6}$ alkenyl, $C_{2-6}$ alkynyl, $C_{3-10}$ cycloalkyl, $C_{6-10}$ aryl, 5- to 10-membered heteroaryl, a 3- to 10-membered non-aromatic heterocyclic group, $C_{1-6}$ alkoxy, $C_{1-6}$ alkylthio, mono-$C_{1-6}$ alkylamino and di-$C_{1-6}$ alkylamino.

(Meaning of Substituent Group D)
The Substituent Group D represents a group consisting of halogen, hydroxyl, mercapto, cyano, formyl, oxo, $C_{1-6}$ alkyl, $C_{3-10}$ cycloalkyl, $C_{1-6}$ alkoxy, amino, mono-$C_{1-6}$ alkylamino, di-$C_{1-6}$ alkylamino, azetidinyl, pyrrolidinyl, piperidinyl, piperazinyl, diazepanyl and a group represented by -$T^4$-$T^5$, wherein $T^4$ represents carbonyl or sulfonyl, and $T^5$ represents $C_{1-6}$ alkyl, $C_{3-10}$ cycloalkyl, azetidinyl, pyrrolidinyl, piperidinyl, hydroxyl, $C_{1-6}$ alkoxy, amino, mono-$C_{1-6}$ alkylamino or di-$C_{1-6}$ alkylamino.

Each group included in Substituent Group D may be substituted with hydroxyl, $C_{1-6}$ alkyl, di-$C_{1-6}$ alkylamino, azetidinyl or pyrrolidinyl.

(Meaning of Substituent Group E)
The Substituent Group E represents a group consisting of methyl, ethyl, dimethylamino, azetidinyl, pyrrolidinyl, piperidinyl and piperazinyl.

Each group included in Substituent Group E may be substituted with hydroxyl, methyl, dimethylamino, azetidinyl, pyrrolidinyl or piperidinyl.

(Meaning of Substituent Group F)
The Substituent Group F represents a group consisting of methyl, ethyl, n-propyl, acetyl, dimethylamino, diethylamino, azetidinyl, pyrrolidinyl and piperazinyl.

Each group included in Substituent Group F may be substituted with methyl or dimethylamino.

(Meaning of Substituent Group G)
The Substituent Group G represents a group consisting of dimethylamino, azetidinyl, pyrrolidinyl, piperidinyl, piperazinyl, dimethylaminomethyl, dimethylaminoethyl, azetidin-1-ylmethyl, pyrrolidin-1-ylmethyl and piperidin-1-ylmethyl.

Each group included in Substituent Group G may be substituted with methyl or dimethylamino.

(Meaning of Substituent Group G-1)
The Substituent Group G-1 represents a group consisting of azetidinyl, pyrrolidinyl, piperidinyl, piperazinyl, dimethylaminomethyl, dimethylaminoethyl, azetidin-1-ylmethyl, pyrrolidin-1-ylmethyl and piperidin-1-ylmethyl.

Each group included in Substituent Group G-1 may be substituted with methyl or dimethylamino.

(Meaning of Substituent Group G-2)
The Substituent Group G-2 represents a group consisting of hydroxyl, methoxy, hydroxymethyl and dimethyl amino acetoxy.

(Meaning of Substituent Group H)

The Substituent Group H represents a group consisting of dimethylamino, diethylamino, dimethylaminoethyl, dimethylaminopropyl and 1-methylazetidin-3-yl.

(Meaning of $R^2$ and $R^3$)

$R^2$ and $R^3$ represent hydrogen.

(Meaning of $R^4$, $R^5$, $R^6$ and $R^7$)

$R^4$, $R^5$, $R^6$ and $R^7$ may be the same or different and each represents hydrogen, halogen, hydroxyl, cyano, trifluoromethyl, $C_{1-6}$ alkyl, $C_{2-6}$ alkenyl, $C_{2-6}$ alkynyl, $C_{1-6}$ alkoxy, amino, mono-$C_{1-6}$ alkylamino, di-$C_{1-6}$ alkylamino or a group represented by the formula —CO—$R^{12}$, wherein $R^{12}$ represents hydrogen, hydroxyl, $C_{1-6}$ alkyl, $C_{1-6}$ alkoxy, amino, mono-$C_{1-6}$ alkylamino or di-$C_{1-6}$ alkylamino.

The preferable example of $R^4$, $R^5$, $R^6$ and $R^7$ includes hydrogen, halogen, $C_{1-6}$ alkyl, $C_{1-6}$ alkoxy and trifluoromethyl.

The more preferable example of $R^4$, $R^5$, $R^6$ and $R^7$ includes hydrogen, halogen and $C_{1-6}$ alkyl.

The even more preferable example of $R^4$, $R^5$, $R^6$ and $R^7$ includes hydrogen, fluorine, chlorine and methyl.

$R^4$, $R^5$, $R^6$ and $R^7$ may be in any one of the following cases: (1) all of them represent hydrogen, (2) all of them represent substituents other than hydrogen, and (3) some of them represent hydrogen and the others represent substituents other than hydrogen. Preferably, 2 to 4 of $R^4$, $R^5$, $R^6$ and $R^7$ represent hydrogen.

Preferable example for a group represented by the formula:

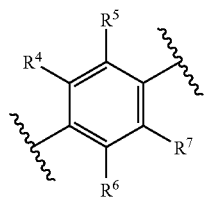

includes groups represented by the formulas:

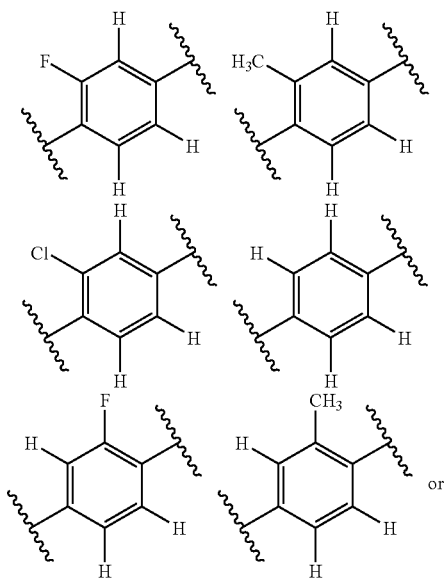

or

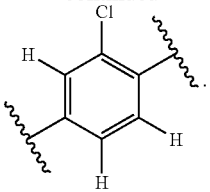

or a group represented by the formula:

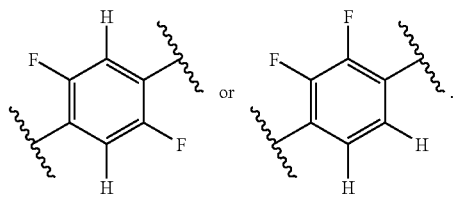

(Meaning of $R^8$)

$R^8$ represents hydrogen or $C_{1-6}$ alkyl.

The preferable example of $R^8$ includes hydrogen.

(Meaning of $R^9$)

$R^9$ represents a 3- to 10-membered non-aromatic heterocyclic group wherein the group is limited to a group having nitrogen as a ring constituent atom and the nitrogen having a bonding hand, or a group represented by the formula —$NR^{11a}R^{11b}$, wherein $R^{11a}$ and $R^{11b}$ represent the same meaning as described above.

$R^9$ may be substituted with a substituent selected from Substituent Group A or Substituent Group B.

The preferable example of $R^9$ includes mono-$C_{1-6}$ alkylamino, mono-$C_{3-10}$ cycloalkylamino, mono-$C_{6-10}$ arylamino, mono-5- to 10-membered heteroarylamino or mono-4- to 10-membered non-aromatic heterocyclic amino, wherein $R^9$ may be substituted with a substituent selected from Substituent Group A or Substituent Group B.

The more preferable example of $R^9$ includes mono-$C_{3-10}$ cycloalkylamino or mono-$C_{6-10}$ arylamino, wherein $R^9$ may be substituted with a substituent selected from Substituent Group A or Substituent Group B.

The even more preferable example of $R^9$ includes mono-$C_{3-10}$ cycloalkylamino or mono-$C_{6-10}$ arylamino, wherein $R^9$ may be substituted with a substituent selected from Substituent Group I.

The Substituent Group I represents a group consisting of halogen, trifluoromethyl, cyano, $C_{1-6}$ alkyl and $C_{1-6}$ alkoxy.

The especially preferable example of $R^9$ includes cyclopentylamino, cyclohexylamino, cycloheptylamino and phenylamino, wherein $R^9$ may be substituted with a substituent selected from Substituent Group I.

The most preferable example of $R^9$ includes phenylamino optionally substituted with a substituent selected from the above Substituent Group I.

(Meaning of n)

n represents an integer of 1 or 2.

The preferable example of n includes 1.

(Meaning of X)

X represents a group represented by the formula —C($R^{10}$)= or nitrogen, wherein $R^{10}$ represents hydrogen, halogen, cyano, $C_{1-6}$ alkyl, $C_{2-6}$ alkenyl, $C_{2-6}$ alkynyl or a group represented by the formula —CO—$R^2$, wherein $R^{12}$ represents the same meaning as described above.

The preferable example of X includes a group represented by the formula —C($R^{10a}$)= or nitrogen, wherein $R^{10a}$ represents hydrogen, halogen or cyano.

The more preferable example of X includes a group represented by the formula —CH= or nitrogen.

The preferable compound of the formula (I) includes a compound obtained by selecting respective aspects of $R^1$, $R^2$, $R^3$, $R^4$, $R^5$, $R^6$, $R^7$, $R^8$, $R^9$, X and n in the compound and combining them arbitrarily.

The preferable compound of the formula (I) includes, other than the compounds described in Examples, the compounds illustrated below; but the present invention is not limited to the compounds described in Examples and the compounds illustrated below.

(1) N-(4-{[2-({[(1-ethylpiperidin-4-yl)(methyl)amino]carbonyl}amino)pyridin-4-yl]oxy}-2-fluorophenyl)-N'-(4-fluorophenyl)cyclopropane-1,1-dicarboxamide, (2) N-(4-{[2-({[(1-ethylpiperidin-4-yl)(methyl)amino]carbonyl}amino)pyridin-4-yl]oxy}phenyl)-N'-(4-fluorophenyl)cyclopropane-1,1-dicarboxamide, (3) N-{2-fluoro-4-[(2-{[(4-methyl-1,4-diazepan-1-yl)carbonyl]amino}pyridin-4-yl)oxy]phenyl}-N'-(4-fluorophenyl)cyclopropane-1,1-dicarboxamide, (4) N-(4-fluorophenyl)-N'-{2-fluoro-4-[(2-{[(3-pyrrolidin-1-ylazetidin-1-yl)carbonyl]amino}pyridin-4-yl)oxy]phenyl}cyclopropane-1,1-dicarboxamide, (5) N-{2-fluoro-4-[(2-{[(4-methylpiperazin-1-yl)carbonyl]amino}pyridin-4-yl)oxy]phenyl}-N'-(4-fluorophenyl)cyclopropane-1,1-dicarboxamide, (6) N-[4-({2-[({4-[2-(dimethylamino)ethyl]-1,4-diazepan-1-yl}carbonyl)amino]pyridin-4-yl}oxy)-2-fluorophenyl]-N'-phenylcyclopropane-1,1-dicarboxamide, (7) N-(4-{[2-({[3-(dimethylamino)azetidin-1-yl]carbonyl}amino)pyridin-4-yl]oxy}-2-fluorophenyl)-N'-(4-fluorophenyl)cyclopropane-1,1-dicarboxamide, (8) N-(4-{[2-({[3-(dimethylamino)azetidin-1-yl]carbonyl}amino)pyridin-4-yl]oxy}phenyl)-N'-(4-fluorophenyl)cyclopropane-1,1-dicarboxamide, (9) N-(4-{[2-({[3-(dimethylamino)azetidin-1-yl]carbonyl}amino)pyridin-4-yl]oxy}-2-fluorophenyl)-N'-phenylcyclopropane-1,1-dicarboxamide,

(10) N-[2-fluoro-4-({2-[({methyl[1-(1-methylazetidin-3-yl)piperidin-4-yl]amino}carbonyl)amino]pyridin-4-yl}oxy)phenyl]-N'-phenylcyclopropane-1,1-dicarboxamide,

(11) N-(2-fluoro-4-{[2-({[4-(1-methylazetidin-3-yl)piperazin-1-yl]carbonyl}amino)pyridin-4-yl]oxy}phenyl)-N'-phenylcyclopropane-1,1-dicarboxamide,

(12) N-(4-fluorophenyl)-N'-(4-{[2-({[4-(1-methylazetidin-3-yl)piperazin-1-yl]carbonyl}amino)pyridin-4-yl]oxy}phenyl)cyclopropane-1,1-dicarboxamide,

(13) N-(2-fluoro-4-{[2-({[(1-methylpiperidin-4-yl)amino]carbonyl}amino)pyridin-4-yl]oxy}phenyl)-N'-(4-fluorophenyl)cyclopropane-1,1-dicarboxamide,

(14) N-{2-fluoro-4-[(2-{[(4-hydroxy-1,4'-bipiperidin-1'-yl)carbonyl]amino}pyridin-4-yl)oxy]phenyl}-N'-phenylcyclopropane-1,1-dicarboxamide,

(15) N-(4-{[2-({[{1-[3-(dimethylamino)propyl]piperidin-4-yl}(methyl)amino]carbonyl}amino)pyridin-4-yl]oxy}-2-fluorophenyl)-N'-phenylcyclopropane-1,1-dicarboxamide,

(16) N-(4-{[2-({[(3-azetidin-1-ylpropyl)(methyl)amino]carbonyl}amino)pyridin-4-yl]oxy}-2-fluorophenyl)-N'-(4-fluorophenyl)cyclopropane-1,1-dicarboxamide,

(17) N-(2-fluoro-4-{[2-({[methyl(3-pyrrolidin-1-ylpropyl)amino]carbonyl}amino)pyridin-4-yl]oxy}phenyl)-N'-(4-fluorophenyl)cyclopropane-1,1-dicarboxamide,

(18) N-(4-{[2-({[[3-(dimethylamino)propyl](methyl)amino]carbonyl}amino)pyridin-4-yl]oxy}-2-fluorophenyl)-N'-(4-fluorophenyl)cyclopropane-1,1-dicarboxamide,

(19) N-(2-fluoro-4-{[2-({[methyl(4-pyrrolidin-1-ylbutyl)amino]carbonyl}amino)pyridin-4-yl]oxy}phenyl)-N'-phenylcyclopropane-1,1-dicarboxamide,

(20) N-[2-fluoro-4-({2-[(morpholin-4-ylcarbonyl)amino]pyridin-4-yl}oxy)phenyl]-N'-(4-fluorophenyl)cyclopropane-1,1-dicarboxamide,

(21) N-[4-({2-[(azetidin-1-ylcarbonyl)amino]pyridin-4-yl}oxy)-2-fluorophenyl]-N'-(4-fluorophenyl)cyclopropane-1,1-dicarboxamide,

(22) N-(2-fluoro-4-{[2-({[methyl(3-morpholin-4-ylpropyl)amino]carbonyl}amino)pyridin-4-yl]oxy}phenyl)-N'-(4-fluorophenyl)cyclopropane-1,1-dicarboxamide,

(23) N-[2-fluoro-4-({2-[({methyl[3-(4-methylpiperazin-1-yl)propyl]amino}carbonyl)amino]pyridin-4-yl}oxy)phenyl]-N'-(4-fluorophenyl)cyclopropane-1,1-dicarboxamide,

(24) N-(4-fluorophenyl)-N'-[2-fluoro-4-({2-[(pyrrolidin-1-ylcarbonyl)amino]pyridin-4-yl}oxy)phenyl]cyclopropane-1,1-dicarboxamide,

(25) N-(2-fluoro-4-{[2-({[methyl(1-methylpiperidin-4-yl)amino]carbonyl}amino)pyridin-4-yl]oxy}phenyl)-N'-2-thienylcyclopropane-1,1-dicarboxamide,

(26) N-(2-fluoro-4-{[2-({[methyl(1-methylpiperidin-4-yl)amino]carbonyl}amino)pyridin-4-yl]oxy}phenyl)-N'-1,3-thiazol-2-ylcyclopropane-1,1-dicarboxamide,

(27) N-(2-fluoro-4-{[2-({[methyl(1-methylpiperidin-4-yl)amino]carbonyl}amino)pyridin-4-yl]oxy}phenyl)-N'-(5-methylisoxazol-3-yl)cyclopropane-1,1-dicarboxamide,

(28) N-(2-fluoro-4-{[2-({[methyl(1-methylpiperidin-4-yl)amino]carbonyl}amino)pyridin-4-yl]oxy}phenyl)-N'-(3-methylisoxazol-5-yl)cyclopropane-1,1-dicarboxamide,

(29) N-{2-fluoro-4-[(2-{[(4-hydroxypiperidin-1-yl)carbonyl]amino}pyridin-4-yl)oxy]phenyl}-N'-(4-fluorophenyl)cyclopropane-1,1-dicarboxamide,

(30) N-{2-fluoro-4-[(2-{[(4-methoxypiperidin-1-yl)carbonyl]amino}pyridin-4-yl)oxy]phenyl}-N'-(4-fluorophenyl)cyclopropane-1,1-dicarboxamide,

(31) N-{2-fluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide,

(32) N-{2-fluoro-4-[(2-{[(3-methoxyazetidin-1-yl)carbonyl]amino}pyridin-4-yl)oxy]phenyl}-N'-(4-fluorophenyl)cyclopropane-1,1-dicarboxamide,

(33) N-(2-fluoro-4-{[2-({[(2-methoxyethyl)(methyl)amino]carbonyl}amino)pyridin-4-yl]oxy}phenyl)-N'-(4-fluorophenyl)cyclopropane-1,1-dicarboxamide,

(34) N-(2-fluoro-4-{[2-({[4-(3-hydroxyazetidin-1-yl)piperidin-1-yl]carbonyl}amino)pyridin-4-yl]oxy}phenyl)-N'-(4-fluorophenyl)cyclopropane-1,1-dicarboxamide,

(35) N-(2-fluoro-4-{[2-({[methyl(tetrahydro-2H-pyran-4-yl)amino]carbonyl}amino)pyridin-4-yl]oxy}phenyl)-N'-(4-fluorophenyl)cyclopropane-1,1-dicarboxamide,

(36) N-(2-fluoro-4-{[2-({[methyl(1-methylpiperidin-3-yl)amino]carbonyl}amino)pyridin-4-yl]oxy}phenyl)-N'-(4-fluorophenyl)cyclopropane-1,1-dicarboxamide,

(37) N-[4-({2-[({3-[(dimethylamino)methyl]piperidin-1-yl}carbonyl)amino]pyridin-4-yl}oxy)phenyl]-N'-(4-fluorophenyl)cyclopropane-1,1-dicarboxamide,

(38) N-[4-({2-[({3-[(dimethylamino)methyl]pyrrolidin-1-yl}carbonyl)amino]pyridin-4-yl}oxy)-2-fluorophenyl]-N'-(4-fluorophenyl)cyclopropane-1,1-dicarboxamide,

(39) N-(2-fluoro-4-{[2-({[methyl(1-methylpyrrolidin-3-yl)amino]carbonyl}amino)pyridin-4-yl]oxy}phenyl)-N'-(4-fluorophenyl)cyclopropane-1,1-dicarboxamide,

(40) N-{2-fluoro-4-[(2-{[(3-hydroxypyrrolidin-1-yl)carbonyl]amino}pyridin-4-yl)oxy]phenyl}-N'-(4-fluorophenyl)cyclopropane-1,1-dicarboxamide,

(41) N-{2-fluoro-4-[(2-{[(3-methoxypyrrolidin-1-yl)carbonyl]amino}pyridin-4-yl)oxy]phenyl}-N'-(4-fluorophenyl)cyclopropane-1,1-dicarboxamide,

(42) N-{4-[(2-{[(3,4-dihydroxypyrrolidin-1-yl)carbonyl]amino}pyridin-4-yl)oxy]-2-fluorophenyl}-N'-(4-fluorophenyl)cyclopropane-1,1-dicarboxamide,

(43) N-{2-fluoro-4-[(2-{[(3-hydroxy-4-methoxypyrrolidin-1-yl)carbonyl]amino}pyridin-4-yl)oxy]phenyl}-N'-(4-fluorophenyl)cyclopropane-1,1-dicarboxamide,

(44) N-{4-[(2-{[(3,4-dimethoxypyrrolidin-1-yl)carbonyl]amino}pyridin-4-yl)oxy]-2-fluorophenyl}-N'-(4-fluorophenyl)cyclopropane-1,1-dicarboxamide,
(45) N-{2-fluoro-4-[(2-{[(3-hydroxypiperidin-1-yl)carbonyl]amino}pyridin-4-yl)oxy]phenyl}-N'-(4-fluorophenyl)cyclopropane-1,1-dicarboxamide,
(46) N-{2-fluoro-4-[(2-{[(3-methoxypiperidin-1-yl)carbonyl]amino}pyridin-4-yl)oxy]phenyl}-N'-(4-fluorophenyl)cyclopropane-1,1-dicarboxamide,
(47) N-(4-{[2-({[3-(dimethylamino)piperidin-1-yl]carbonyl}amino)pyridin-4-yl]oxy}-2-fluorophenyl)-N'-(4-fluorophenyl)cyclopropane-1,1-dicarboxamide The more preferable compound of the formula (I) includes the compounds illustrated below;
(1) N-[4-({2-[({4-[2-(Dimethylamino)ethyl]piperazin-1-yl}carbonyl)amino]pyridin-4-yl}oxy)-2-fluorophenyl]-N'-(4-fluorophenyl)cyclopropane-1,1-dicarboxamide,
(2) N-(2-Fluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide,
(3) N-(4-Fluorophenyl)-N'-{2-fluoro-4-[(2-{[(4-pyrrolidin-1-ylpiperidin-1-yl)carbonyl]amino}pyridin-4-yl)oxy]phenyl}cyclopropane-1,1-dicarboxamide,
(4) N-[4-({2-[({4-[(Dimethylamino)methyl]piperidin-1-yl}carbonyl)amino]pyridin-4-yl}oxy)-2-fluorophenyl]-N'-(4-fluorophenyl)cyclopropane-1,1-dicarboxamide,
(5) N-{4-[(2-{[(4-Azetidin-1-ylpiperidin-1-yl)carbonyl]amino}pyridin-4-yl)oxy]-2-fluorophenyl}-N'-(4-fluorophenyl)cyclopropane-1,1-dicarboxamide,
(6) N-[4-({2-[({4-[3-(Dimethylamino)azetidin-1-yl]piperidin-1-yl}carbonyl)amino]pyridin-4-yl}oxy)-2-fluorophenyl]-N'-(4-fluorophenyl)cyclopropane-1,1-dicarboxamide,
(7) N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide,
(8) N-(2-Fluoro-4-{[2-({[4-(1-methylpiperidin-4-yl)piperazin-1-yl]carbonyl}amino)pyridin-4-yl]oxy}phenyl)-N'-(4-fluorophenyl)cyclopropane-1,1-dicarboxamide,
(9) N-(2-Fluoro-4-{[2-({[4-(1-methylazetidin-3-yl)piperazin-1-yl]carbonyl}amino)pyridin-4-yl]oxy}phenyl)-N'-(4-fluorophenyl)cyclopropane-1,1-dicarboxamide,
(10) N-(4-{[2-({[4-(Dimethylamino)piperidin-1-yl]carbonyl}amino)pyridin-4-yl]oxy}-2-fluorophenyl)-N'-(4-fluorophenyl)cyclopropane-1,1-dicarboxamide,
(11) N-(4-{[2-({[4-(Azetidin-1-ylmethyl)piperidin-1-yl]carbonyl}amino)pyridin-4-yl]oxy}-2-fluorophenyl)-N'-(4-fluorophenyl)cyclopropane-1,1-dicarboxamide,
(12) N-(4-Fluorophenyl)-N'-(2-fluoro-4-{[2-({[4-(pyrrolidin-1-ylmethyl)piperidin-1-yl]carbonyl}amino)pyridin-4-yl]oxy}phenyl)cyclopropane-1,1-dicarboxamide,
(13) N-(4-{[2-({[(3S)-3-(Dimethylamino)pyrrolidin-1-yl]carbonyl}amino)pyridin-4-yl]oxy}-2-fluorophenyl)-N'-(4-fluorophenyl)cyclopropane-1,1-dicarboxamide,
(14) N-(4-{[2-({[(3R)-3-(Dimethylamino)pyrrolidin-1-yl]carbonyl}amino)pyridin-4-yl]oxy}-2-fluorophenyl)-N'-(4-fluorophenyl)cyclopropane-1,1-dicarboxamide,
(15) N-(2-Fluoro-4-{[2-({[methyl(1-methylpiperidin-4-yl)amino]carbonyl}amino)pyridin-4-yl]oxy}phenyl)-N'-phenylcyclopropane-1,1-dicarboxamide,
(16) N-(2-Fluoro-4-{[2-({[4-(4-methylpiperazin-1-yl)piperidin-1-yl]carbonyl}amino)pyridin-4-yl]oxy}phenyl)-N'-phenylcyclopropane-1,1-dicarboxamide,
(17) N-[4-({2-[({4-[3-(Dimethylamino)azetidin-1-yl]piperidin-1-yl}carbonyl)amino]pyridin-4-yl}oxy)-2-fluorophenyl]-N'-phenylcyclopropane-1,1-dicarboxamide,
(18) N-(4-{[2-({[(1-Ethylpiperidin-4-yl)(methyl)amino]carbonyl}amino)pyridin-4-yl]oxy}-2-fluorophenyl)-N'-phenylcyclopropane-1,1-dicarboxamide,
(19) N-[4-({2-[(Azetidin-1-ylcarbonyl)amino]pyridin-4-yl}oxy)-2-fluorophenyl]-N'-(4-fluorophenyl)cyclopropane-1,1-dicarboxamide,
(20) N-(4-Fluorophenyl)-N'-[2-fluoro-4-({2-[(pyrrolidin-1-ylcarbonyl)amino]pyridin-4-yl}oxy)phenyl]cyclopropane-1,1-dicarboxamide,
(21) N-{2-Fluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide,
(22) N-[4-({2-[(1,3'-Biazetidin-1'-ylcarbonyl)amino]pyridin-4-yl}oxy)-2-fluorophenyl]-N'-(4-fluorophenyl)cyclopropane-1,1-dicarboxamide,
(23) N-(2-Fluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide,
(24) N-(4-{[2-({[3-(Dimethylamino)azetidin-1-yl]carbonyl}amino)pyridin-4-yl]oxy}-2-fluorophenyl)-N'-(4-fluorophenyl)cyclopropane-1,1-dicarboxamide,
(25) N-[4-({2-[({3-[(Dimethylamino)methyl]azetidin-1-yl}carbonyl)amino]pyridin-4-yl}oxy)-2-fluorophenyl]-N'-(4-fluorophenyl)cyclopropane-1,1-dicarboxamide,
(26) N-{2-Fluoro-4-[(2-{[(4-hydroxypiperidin-1-yl)carbonyl]amino}pyridin-4-yl)oxy]phenyl}-N'-(4-fluorophenyl)cyclopropane-1,1-dicarboxamide,
(27) N-(2-Fluoro-4-{[2-({[4-(hydroxymethyl)piperidin-1-yl]carbonyl}amino)pyridin-4-yl]oxy}phenyl)-N'-(4-fluorophenyl)cyclopropane-1,1-dicarboxamide,
(28) N-(2-Fluoro-4-{[2-({[(3R)-3-hydroxypyrrolidin-1-yl]carbonyl}amino)pyridin-4-yl]oxy}phenyl)-N'-(4-fluorophenyl)cyclopropane-1,1-dicarboxamide,
(29) N-(2-Fluoro-4-{[2-({[(3S)-3-hydroxypyrrolidin-1-yl]carbonyl}amino)pyridin-4-yl]oxy}phenyl)-N'-(4-fluorophenyl)cyclopropane-1,1-dicarboxamide,
(30) N-[4-({2-[(Azetidin-1-ylcarbonyl)amino]pyridin-4-yl}oxy)-2,5-difluorophenyl]-N'-(4-fluorophenyl)cyclopropane-1,1-dicarboxamide,
(31) N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide,
(32) N-(2,5-Difluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide,
(33) N-[2,5-Difluoro-4-({2-[({3-[(dimethylamino)methyl]azetidin-1-yl}carbonyl)amino]pyridin-4-yl}oxy)phenyl]-N'-(4-fluorophenyl)cyclopropane-1,1-dicarboxamide,
(34) N-(2,5-Difluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide,
(35) N-{4-[(2-{[3-(Azetidin-1-ylmethyl)azetidin-1-ylcarbonyl]amino}pyridin-4-yl)oxy]-2,5-difluorophenyl}-N'-(4-fluorophenyl)cyclopropane-1,1-dicarboxamide,
(36) N-(2,5-Difluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide,
(37) N-{2,5-Difluoro-4-[(4-{[(3-hydroxyazetidin-1-yl)carbonyl]amino}pyrimidin-6-yl)oxy]phenyl}-N'-(4-fluorophenyl)cyclopropane-1,1-dicarboxamide,
(38) N-[4-({4-[({3-[(Dimethylamino)methyl]azetidin-1-yl}carbonyl)amino]pyrimidin-6-yl}oxy)-2,5-difluorophenyl]-N'-(4-fluorophenyl)cyclopropane-1,1-dicarboxamide,
(39) N-(2,5-Difluoro-4-{[4-({[3-(hydroxymethyl)azetidin-1-yl]carbonyl}amino)pyrimidin-6-yl]oxy}phenyl)-N'-(4-fluorophenyl)cyclopropane-1,1-dicarboxamide,
(40) N-(2,5-Difluoro-4-{[4-({[methyl(1-methylpiperidin-4-yl)amino]carbonyl}amino)pyrimidin-6-yl]oxy}phenyl)-N'-(4-fluorophenyl)cyclopropane-1,1-dicarboxamide,
(41) N-(2,5-Difluoro-4-{[4-({[4-(4-methylpiperazin-1-yl)piperidin-1-yl]carbonyl}amino)pyrimidin-6-yl]oxy}phenyl)-N'-(4-fluorophenyl)cyclopropane-1,1-dicarboxamide,
(42) N-(4-{[2-({[4-(Dimethylamino)piperidin-1-yl]carbonyl}amino)pyridin-4-yl]oxy}-2,5-difluorophenyl)-N'-(4-fluorophenyl)cyclopropane-1,1-dicarboxamide,

(43) N-{2,5-Difluoro-4-[(2-{[(4-methylpiperazin-1-yl)carbonyl]amino}pyridin-4-yl]oxy}phenyl)-N'-(4-fluorophenyl)cyclopropane-1,1-dicarboxamide,
(44) N-{2,5-Difluoro-4-[(2-{[(4-hydroxypiperidin-1-yl)carbonyl]amino}pyridin-4-yl)oxy]phenyl}-N'-(4-fluorophenyl)cyclopropane-1,1-dicarboxamide,
(45) N-{4-[(2-{[(4-Azetidin-1-ylpiperidin-1-yl)carbonyl]amino}pyridin-4-yl)oxy]oxy}-2,5-difluorophenyl}-N'-(4-fluorophenyl)cyclopropane-1,1-dicarboxamide,
(46) N-(2,5-Difluoro-4-{[2-({[3-(2-dimethylaminoacetoxy)azetidin-1-yl]carbonyl}amino)pyridin-4-yl]oxy}phenyl)-N'-(4-fluorophenyl)cyclopropane-1,1-dicarboxamide,
(47) N-(2,5-Difluoro-4-{[2-({[(3S)-3-hydroxypyrrolidin-1-yl]carbonyl}amino)pyridin-4-yl]oxy}phenyl)-N'-(4-fluorophenyl)cyclopropane-1,1-dicarboxamide,
(48) N-(2,5-Difluoro-4-{[2-({[(3R)-3-hydroxypyrrolidin-1-yl]carbonyl}amino)pyridin-4-yl]oxy}phenyl)-N'-(4-fluorophenyl)cyclopropane-1,1-dicarboxamide.

The still more preferable compound of the formula (I) includes the compounds illustrated below;
(1) N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide
(2) N-[4-({2-[(Azetidin-1-ylcarbonyl)amino]pyridin-4-yl}oxy)-2-fluorophenyl]-N'-(4-fluorophenyl)cyclopropane-1,1-dicarboxamide
(3) N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide
(4) N-(2,5-Difluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide
(5) N-(2,5-Difluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide
(6) N-(2,5-Difluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide.

The phrase "may be substituted with a substituent selected from Substituent Group" or "optionally substituted with a substituent selected from Substituent Group" means "may be substituted with 1 to 3 substituents selected arbitrarily from the substituents described in the Substituent Group."

The compounds of the present invention can be produced based on the description of WO 2007/023768.

EXAMPLE

Pharmacological Test Example

WO 2007/023768 has confirmed that the compound of the present invention has inhibitory activity against hepatocyte growth factor receptor, anti-tumor activity, inhibitory activity against angiogenesis, and inhibitory activity against cancer metastasis. The activity against esophageal cancer of the compound of the present invention was evaluated based on the following methods.

Abbreviations and terms used in the following Pharmacological Test Examples are listed as follows:
(Abbreviation List)
FBS (Fetal bovine serum)

Pharmacological Text Example 1

An Inhibitory Action Against Proliferation of Human Esophageal Cancer Cells

Human esophageal cancer cells (OE19, OE21 and OE33) were purchased from Dainippon Sumitomo Pharma Co., Ltd. OE19, OE21 or was suspended in RPMI1640 medium (purchased from Sigma) containing 10% FBS. The cell suspension ($2 \times 10^4$ cells/ml) was dispensed into a 96-well plate (purchased from FALCON; product No. 353075) by 0.1 ml/well, and incubated at 37° C. in a 5% $CO_2$ incubator overnight. After the incubation, 0.1 ml of the test substance diluted with RPMI1640 medium containing 10% FBS was added to each well, which was further incubated for 3 days in the 5% $CO_2$ incubator (37° C.). After the incubation, 10 μl of Cell Counting Kit-8 (purchased from DOJINDO Laboratories) was added to each well, which were incubated for about 2 hours in the 5% $CO_2$ incubator (37° C.). After the incubation, the absorbance of the each well was measured using a plate reader MTP-500 (Corona Electric Co., Ltd) with a measurement wavelength of 450 nm and a control wavelength of 660 nm. A ratio of absorbance (%) of each well with the test substance against the wells without the test substance was determined, and based on this ratio, the concentration of the test substance required to inhibit 50% of cell proliferation ($IC_{50}$; μM) was determined and the results are shown in Table 1.

TABLE 1

| Test Substance | 0E33 | 0E19 | 0E21 |
|---|---|---|---|
| N-(2-Fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide | 1.6 | 3.6 | 5.5 |
| N-[4-({2-[(Azetidin-1-ylcarbonyl)amino]pyridin-4-yl}oxy)-2-fluorophenyl]-N'-(4-fluorophenyl)cyclopropane-1,1-dicarboxamide | 0.18 | 4.2 | >10 |
| N-{2,5-Difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide | 0.24 | 5.2 | 6.4 |
| N-(2,5-Difluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide | 0.67 | 3.5 | 3.0 |
| N-(2,5-Difluoro-4-{[2-({[methyl(1-methylpiperidin-4-yl)amino]carbonyl}amino)pyridin-4-yl]oxy}phenyl)-N'-(4-fluorophenyl)cyclopropane-1,1-dicarboxamide | 0.14 | 2.3 | 1.7 |
| N-(2,5-Difluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide | 0.25 | 3.2 | 7.4 |

INDUSTRIAL APPLICABILITY

The compound of the present invention has excellent inhibitory action against HGFR and useful as a pharmaceutical composition for treating esophageal cancer.

The invention claimed is:

1. A method of treating esophageal cancer, comprising the step of administering to a patient suffering from esophageal cancer, a compound or a salt thereof,
   wherein the compound is selected from the group consisting of:
   N-(2-fluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide,
   N-[4-({2-[(azetidin-1-ylcarbonyl)amino]pyridin-4-yl}oxy)-2-fluorophenyl]-N'-(4-fluorophenyl)cyclopropane-1,1-dicarboxamide,
   N-{2,5-difluoro-4-[(2-{[(3-hydroxyazetidin-1-yl)carbonyl]amino}pyridin-4-yl)oxy]phenyl}-N'-(4-fluorophenyl)cyclopropane-1,1-dicarboxamide,
   N-(2,5-difluoro-4-{[2-({[4-(4-methylpiperazin-1-yl)piperidin-1-yl]carbonyl}amino)pyridin-4-yl]oxy}phenyl)-N'-(4-fluorophenyl)cyclopropane-1,1-dicarboxamide,
   N-(2,5-difluoro-4-{[2-({[methyl(1-methylpiperidin-4-yl)amino]carbonyl}amino)pyridin-4-yl]oxy}phenyl)-N'-(4-fluoropheny)cyclopropane-1,1-dicarboxamide, and
   N-(2,5-difluoro-4-{[2-({[3-(hydroxymethyl)azetidin-1-yl]carbonyl}amino)pyridin-4-yl]oxy}phenyl)-N'-(4-fluorophenyl)cyclopropane-1,1-dicarboxamide.

* * * * *